(12) United States Patent
Reitblat et al.

(10) Patent No.: US 12,127,949 B1
(45) Date of Patent: Oct. 29, 2024

(54) PERCUTANEOUS POSTERIOR SPINAL FUSION IMPLANT CONSTRUCTION AND METHOD

(71) Applicant: Stryker European Operations Holdings LLC, Kalamazoo, MI (US)

(72) Inventors: Abram Reitblat, Monroe, NY (US); Steven Krause, Oakland, NJ (US); Charles L. Bush, Jr., Wayne, NJ (US); Douglas Pedrick, Newburgh, NY (US); Lori Dombrowski, Elmwood Park, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 1016 days.

(21) Appl. No.: 17/085,627

(22) Filed: Oct. 30, 2020

Related U.S. Application Data

(63) Continuation of application No. 16/185,848, filed on Nov. 9, 2018, now abandoned, which is a
(Continued)

(51) Int. Cl.
*A61F 2/44* (2006.01)
(52) U.S. Cl.
CPC .................................. *A61F 2/4455* (2013.01)
(58) Field of Classification Search
CPC ............ A61B 17/7074; A61B 17/7076; A61B 17/7077; A61B 17/7079; A61B 17/708;
(Continued)

(56) References Cited

U.S. PATENT DOCUMENTS 3,788,318 A    1/1974    Kim et al.
3,789,852 A    2/1974    Kim et al.
(Continued)

FOREIGN PATENT DOCUMENTS

DE    3711091    10/1988
DE    4238339 A1    5/1994
(Continued)

OTHER PUBLICATIONS

Abram Reitblat et al., U.S. Appl. No. 14/034,021, filed Sep. 23, 2013.
(Continued)

*Primary Examiner* — Si Ming Ku
(74) *Attorney, Agent, or Firm* — Lerner David LLP

(57) ABSTRACT

A system includes tubular members removably positionable over a passageway device connected to a connecting element attached to a vertebra. The tubular members may each include a sidewall having an opening positionable adjacent a proximal end of the passageway device when the tubular member is positioned over the passageway device. The tubular members include channels therein to receive respective blades of the passageway devices. One of the tubular members may be a counter torque tube, and another two of the tubular members may be a hinge shaft and a ball shaft, respectively, of a compression and distraction system. The blades of each passageway device may be integrally formed with a cage of the connecting element to form a monolithic blade-screw. The blades of the monolithic blade-screw may be constructed by affixing distal ends of non-threaded blade extensions to proximal ends of threaded reduction portions integrally connected to the cage.

18 Claims, 15 Drawing Sheets

Related U.S. Application Data continuation of application No. 14/099,104, filed on Dec. 6, 2013, now Pat. No. 10,159,579.

(58) Field of Classification Search
CPC ............ A61B 17/7083; A61B 17/7085; A61B 17/7086; A61B 17/7091; A61F 2/4455
See application file for complete search history.

(56) References Cited

U.S. PATENT DOCUMENTS

| | | |
|---|---|---|
| 3,892,232 A | 7/1975 | Neufeld |
| 3,997,138 A | 12/1976 | Crock et al. |
| 4,269,184 A | 5/1981 | Montgomery |
| 4,350,151 A | 9/1982 | Scott |
| 4,382,438 A | 5/1983 | Jacobs |
| 4,409,968 A | 10/1983 | Drummond |
| 4,411,259 A | 10/1983 | Drummond |
| 4,448,191 A | 5/1984 | Rodnyansky et al. |
| 4,449,532 A | 5/1984 | Storz |
| 4,545,374 A | 10/1985 | Jacobson |
| 4,562,832 A | 1/1986 | Wilder et al. |
| 4,611,581 A | 9/1986 | Steffee |
| 4,733,657 A | 3/1988 | Kluger |
| 4,790,297 A | 12/1988 | Luque |
| 4,817,587 A | 4/1989 | Janese |
| 4,862,891 A | 9/1989 | Smith |
| 4,899,729 A | 2/1990 | Gill et al. |
| 4,913,134 A | 4/1990 | Luque |
| 4,957,495 A | 9/1990 | Kluger |
| 4,984,564 A | 1/1991 | Yuen |
| 5,010,879 A | 4/1991 | Moriya et al. |
| 5,027,793 A | 7/1991 | Engelhardt et al. |
| 5,035,232 A | 7/1991 | Lutze et al. |
| 5,059,194 A | 10/1991 | Michelson |
| 5,125,396 A | 6/1992 | Ray |
| 5,139,487 A | 8/1992 | Baber |
| 5,167,662 A | 12/1992 | Hayes et al. |
| 5,171,279 A | 12/1992 | Mathews |
| 5,183,464 A | 2/1993 | Dubrul et al. |
| 5,195,541 A | 3/1993 | Obenchain |
| 5,197,971 A | 3/1993 | Bonutti |
| 5,219,349 A | 6/1993 | Krag et al. |
| 5,242,443 A | 9/1993 | Kambin |
| 5,281,223 A | 1/1994 | Ray |
| 5,293,863 A | 3/1994 | Zhu et al. |
| 5,295,994 A | 3/1994 | Bonutti |
| D346,217 S | 4/1994 | Sparker et al. |
| 5,312,417 A | 5/1994 | Wilk |
| 5,357,983 A | 10/1994 | Mathews |
| 5,377,667 A | 1/1995 | Patton et al. |
| 5,381,788 A | 1/1995 | Matula et al. |
| 5,385,565 A | 1/1995 | Ray |
| 5,395,317 A | 3/1995 | Kambin |
| 5,409,488 A | 4/1995 | Ulrich |
| 5,425,732 A | 6/1995 | Ulrich |
| 5,439,464 A | 8/1995 | Shapiro |
| 5,454,365 A | 10/1995 | Bonutti |
| 5,464,011 A | 11/1995 | Bridge |
| 5,478,340 A | 12/1995 | Kluger |
| 5,480,440 A | 1/1996 | Kambin |
| 5,487,743 A | 1/1996 | Laurain et al. |
| 5,496,322 A | 3/1996 | Mathews |
| 5,545,228 A | 8/1996 | Kambin |
| 5,569,248 A | 10/1996 | Mathews |
| 5,569,290 A | 10/1996 | McAfee |
| 5,584,887 A | 12/1996 | Kambin |
| 5,591,167 A | 1/1997 | Laurain et al. |
| 5,601,562 A | 2/1997 | Wolf et al. |
| 5,601,590 A | 2/1997 | Bonutti et al. |
| 5,707,359 A | 1/1998 | Bufalini |
| 5,720,751 A | 2/1998 | Jackson |
| 5,728,046 A | 3/1998 | Mayer et al. |
| 5,728,097 A | 3/1998 | Mathews |
| 5,741,261 A | 4/1998 | Moskovitz et al. |
| 5,743,907 A | 4/1998 | Asher et al. |
| 5,746,720 A | 5/1998 | Stouder, Jr. |
| 5,762,629 A | 6/1998 | Kambin |
| 5,772,594 A | 6/1998 | Barrick |
| 5,792,044 A | 8/1998 | Foley et al. |
| 5,795,289 A | 8/1998 | Wyttenbach |
| 5,846,193 A | 12/1998 | Wright |
| 5,882,344 A | 3/1999 | Stouder, Jr. |
| 5,885,291 A | 3/1999 | Moskovitz et al. |
| 5,885,292 A | 3/1999 | Moskovitz et al. |
| 5,891,147 A | 4/1999 | Moskovitz et al. |
| 5,902,231 A | 5/1999 | Foley et al. |
| RE36,221 E | 6/1999 | Breard et al. |
| 5,928,139 A | 7/1999 | Koros et al. |
| 5,944,658 A | 8/1999 | Koros et al. |
| 5,954,635 A | 9/1999 | Foley et al. |
| 5,957,888 A | 9/1999 | Hinchliffe |
| 5,961,499 A | 10/1999 | Bonutti et al. |
| 5,964,761 A | 10/1999 | Kambin |
| 5,976,146 A | 11/1999 | Ogawa et al. |
| 6,007,487 A | 12/1999 | Foley et al. |
| 6,033,406 A | 3/2000 | Mathews |
| 6,036,692 A | 3/2000 | Burel et al. |
| 6,074,391 A | 6/2000 | Metz-Stavenhagen et al. |
| 6,080,156 A | 6/2000 | Asher et al. |
| 6,090,113 A | 7/2000 | Le Couedic et al. |
| 6,123,707 A | 9/2000 | Wagner |
| 6,127,597 A | 10/2000 | Beyar et al. |
| 6,146,386 A | 11/2000 | Blackman et al. |
| 6,152,871 A | 11/2000 | Foley et al. |
| 6,159,179 A | 12/2000 | Simonson |
| 6,162,170 A | 12/2000 | Foley et al. |
| 6,175,758 B1 | 1/2001 | Kambin |
| 6,176,823 B1 | 1/2001 | Foley et al. |
| 6,183,472 B1 | 2/2001 | Lutz |
| 6,187,000 B1 | 2/2001 | Davison et al. |
| 6,197,002 B1 | 3/2001 | Peterson |
| 6,200,322 B1 | 3/2001 | Branch et al. |
| 6,206,822 B1 | 3/2001 | Foley et al. |
| 6,206,826 B1 | 3/2001 | Mathews et al. |
| 6,217,509 B1 | 4/2001 | Foley et al. |
| 6,226,548 B1 | 5/2001 | Foley et al. |
| 6,235,028 B1 | 5/2001 | Brumfield et al. |
| 6,287,313 B1 | 9/2001 | Sasso |
| 6,338,730 B1 | 1/2002 | Bonutti et al. |
| 6,358,266 B1 | 3/2002 | Bonutti |
| 6,371,968 B1 | 4/2002 | Kogasaka et al. |
| 6,425,859 B1 | 7/2002 | Foley et al. |
| 6,475,218 B2 | 11/2002 | Gournay et al. |
| 6,485,518 B1 | 11/2002 | Cornwall et al. |
| 6,506,151 B2 | 1/2003 | Estes et al. |
| 6,520,907 B1 | 2/2003 | Foley et al. |
| 6,524,320 B2 | 2/2003 | DiPoto |
| 6,530,926 B1 | 3/2003 | Davison |
| 6,530,929 B1 | 3/2003 | Justis et al. |
| 6,558,386 B1 | 5/2003 | Cragg |
| 6,558,390 B2 | 5/2003 | Cragg |
| 6,562,046 B2 | 5/2003 | Sasso |
| 6,575,979 B1 | 6/2003 | Cragg |
| 6,596,008 B1 | 7/2003 | Kambin |
| 6,605,095 B2 | 8/2003 | Grossman |
| 6,607,530 B1 | 8/2003 | Carl et al. |
| 6,613,050 B1 | 9/2003 | Wagner et al. |
| 6,616,666 B1 | 9/2003 | Michelson |
| 6,616,667 B1 | 9/2003 | Steiger et al. |
| 6,652,553 B2 | 11/2003 | Davison et al. |
| 6,660,006 B2 | 12/2003 | Markworth et al. |
| 6,692,434 B2 | 2/2004 | Ritland |
| 6,692,473 B2 | 2/2004 | St. Cyr et al. |
| 6,712,818 B1 | 3/2004 | Michelson |
| 6,723,095 B2 | 4/2004 | Hammerslag |
| 6,740,089 B2 | 5/2004 | Haider |
| 6,740,090 B1 | 5/2004 | Cragg et al. |
| 6,746,449 B2 | 6/2004 | Jones et al. |
| 6,749,614 B2 | 6/2004 | Teitelbaum et al. |
| 6,770,074 B2 | 8/2004 | Michelson |
| 6,772,765 B2 | 8/2004 | Scheller et al. |
| 6,790,210 B1 | 9/2004 | Cragg et al. |
| 6,793,656 B1 | 9/2004 | Mathews |
| 6,800,084 B2 | 10/2004 | Davison et al. |

(56) References Cited

U.S. PATENT DOCUMENTS

| | | |
|---|---|---|
| 6,811,558 B2 | 11/2004 | Davison et al. |
| 6,821,277 B2 | 11/2004 | Teitelbaum |
| 6,837,891 B2 | 1/2005 | Davison et al. |
| 6,849,064 B2 | 2/2005 | Hamada |
| 6,923,811 B1 | 8/2005 | Carl et al. |
| 6,929,647 B2 | 8/2005 | Cohen |
| 7,008,422 B2 | 3/2006 | Foley et al. |
| 7,011,660 B2 | 3/2006 | Sherman et al. |
| 7,083,621 B2 | 8/2006 | Shaolian et al. |
| 7,160,300 B2 | 1/2007 | Jackson |
| 7,188,626 B2 | 3/2007 | Foley et al. |
| 7,250,052 B2 | 7/2007 | Landry et al. |
| 7,261,714 B2 | 8/2007 | Richelsoph |
| 7,306,603 B2 | 12/2007 | Boehm, Jr. et al. |
| 7,470,279 B2 | 12/2008 | Jackson |
| 7,578,822 B2 | 8/2009 | Rezach et al. |
| 7,621,918 B2 | 11/2009 | Jackson |
| 7,651,502 B2 | 1/2010 | Jackson |
| 7,666,188 B2 | 2/2010 | Anderson et al. |
| 7,758,617 B2 | 7/2010 | Iott et al. |
| 7,811,288 B2 | 10/2010 | Jones et al. |
| 7,842,073 B2 | 11/2010 | Richelsoph et al. |
| 7,862,587 B2 | 1/2011 | Jackson |
| 7,914,536 B2 | 3/2011 | MacDonald et al. |
| 7,955,355 B2 | 6/2011 | Chin |
| 7,985,242 B2 | 7/2011 | Forton et al. |
| 7,988,713 B2 | 8/2011 | Metz-Stavenhagen |
| 8,002,798 B2 | 8/2011 | Chin et al. |
| 8,002,802 B2 | 8/2011 | Abdou |
| 8,052,720 B2 | 11/2011 | Kuester et al. |
| 8,066,739 B2 | 11/2011 | Jackson |
| 8,075,599 B2 | 12/2011 | Johnson et al. |
| 8,105,361 B2 | 1/2012 | Anderson et al. |
| 8,118,737 B2 | 2/2012 | Perez-Cruet et al. |
| 8,152,810 B2 | 4/2012 | Jackson |
| 8,157,809 B2 | 4/2012 | Butters et al. |
| 8,162,952 B2 | 4/2012 | Cohen et al. |
| 8,177,817 B2 | 5/2012 | Fallin |
| 8,192,440 B2 | 6/2012 | Jones et al. |
| 8,197,488 B2 | 6/2012 | Sorrenti et al. |
| 8,231,635 B2 | 7/2012 | Sharifi-Mehr et al. |
| 8,262,662 B2 | 9/2012 | Beardsley et al. |
| 8,287,546 B2 | 10/2012 | King et al. |
| 8,388,659 B1 | 3/2013 | Lab et al. |
| 8,403,940 B2 | 3/2013 | Parker et al. |
| 8,506,574 B2 | 8/2013 | Butters et al. |
| 8,523,916 B2 | 9/2013 | Anderson et al. |
| 8,894,655 B2 | 11/2014 | Fallin et al. |
| 9,125,694 B2 | 9/2015 | Butler et al. |
| 9,198,692 B1 | 12/2015 | Doose et al. |
| 9,402,661 B2 | 8/2016 | Reitblat et al. |
| 9,510,875 B2 | 12/2016 | Reitblat et al. |
| 2001/0011170 A1 | 8/2001 | Davison et al. |
| 2001/0027320 A1 | 10/2001 | Sasso |
| 2001/0029353 A1 | 10/2001 | Peterson |
| 2001/0049498 A1 | 12/2001 | Davison et al. |
| 2001/0049527 A1 | 12/2001 | Cragg |
| 2001/0053915 A1 | 12/2001 | Grossman |
| 2002/0016583 A1 | 2/2002 | Cragg |
| 2002/0045904 A1 | 4/2002 | Fuss et al. |
| 2002/0068975 A1 | 6/2002 | Teitelbaum et al. |
| 2002/0082598 A1 | 6/2002 | Teitelbaum |
| 2002/0082600 A1 | 6/2002 | Shaolian et al. |
| 2002/0107519 A1 | 8/2002 | Dixon et al. |
| 2002/0116006 A1 | 8/2002 | Cohen |
| 2002/0161368 A1 | 10/2002 | Foley et al. |
| 2002/0173796 A1 | 11/2002 | Cragg |
| 2002/0198526 A1 | 12/2002 | Shaolian et al. |
| 2003/0004517 A1 | 1/2003 | Anderson |
| 2003/0055430 A1 | 3/2003 | Kim |
| 2003/0060826 A1 | 3/2003 | Foley et al. |
| 2003/0073998 A1 | 4/2003 | Pagliuca et al. |
| 2003/0083688 A1 | 5/2003 | Simonson |
| 2003/0130659 A1 | 7/2003 | Haider |
| 2003/0139648 A1 | 7/2003 | Foley et al. |
| 2003/0187436 A1 | 10/2003 | Bolger et al. |
| 2003/0195518 A1 | 10/2003 | Cragg |
| 2003/0199871 A1 | 10/2003 | Foley et al. |
| 2003/0199872 A1 | 10/2003 | Markworth et al. |
| 2003/0199884 A1 | 10/2003 | Davison et al. |
| 2003/0204189 A1 | 10/2003 | Cragg |
| 2003/0208202 A1 | 11/2003 | Falahee |
| 2003/0225408 A1 | 12/2003 | Nichols et al. |
| 2003/0229353 A1 | 12/2003 | Cragg |
| 2004/0006341 A1 | 1/2004 | Shaolian et al. |
| 2004/0006344 A1 | 1/2004 | Nguyen et al. |
| 2004/0034351 A1 | 2/2004 | Sherman et al. |
| 2004/0039384 A1 | 2/2004 | Boehm et al. |
| 2004/0059333 A1 | 3/2004 | Carl et al. |
| 2004/0082954 A1 | 4/2004 | Teitelbaum et al. |
| 2004/0082960 A1 | 4/2004 | Davison |
| 2004/0082961 A1 | 4/2004 | Teitelbaum |
| 2004/0087950 A1 | 5/2004 | Teitelbaum |
| 2004/0093001 A1 | 5/2004 | Hamada |
| 2004/0106934 A1 | 6/2004 | Grossman |
| 2004/0133201 A1 | 7/2004 | Shluzas et al. |
| 2004/0138662 A1 | 7/2004 | Landry et al. |
| 2004/0143265 A1 | 7/2004 | Landry et al. |
| 2004/0143268 A1 | 7/2004 | Falahee |
| 2004/0147928 A1 | 7/2004 | Landry et al. |
| 2004/0147936 A1 | 7/2004 | Rosenberg et al. |
| 2004/0162560 A1 | 8/2004 | Raynor et al. |
| 2004/0172022 A1 | 9/2004 | Landry et al. |
| 2004/0176763 A1 | 9/2004 | Foley et al. |
| 2004/0194791 A1 | 10/2004 | Sterman et al. |
| 2004/0215190 A1 | 10/2004 | Nguyen et al. |
| 2004/0215193 A1 | 10/2004 | Shaolian et al. |
| 2004/0236317 A1 | 11/2004 | Davison |
| 2004/0254576 A1 | 12/2004 | Dunbar et al. |
| 2004/0260287 A1 | 12/2004 | Ferree |
| 2005/0010220 A1 | 1/2005 | Casutt et al. |
| 2005/0010221 A1 | 1/2005 | Dalton |
| 2005/0021030 A1 | 1/2005 | Pagliuca et al. |
| 2005/0021031 A1 | 1/2005 | Foley et al. |
| 2005/0021040 A1 | 1/2005 | Bertagnoli |
| 2005/0025771 A1 | 2/2005 | Wagner et al. |
| 2005/0033297 A1 | 2/2005 | Davison |
| 2005/0038432 A1 | 2/2005 | Shaolian et al. |
| 2005/0038434 A1 | 2/2005 | Mathews |
| 2005/0038436 A1 | 2/2005 | Michelson |
| 2005/0043741 A1 | 2/2005 | Michelson |
| 2005/0043742 A1 | 2/2005 | Bruneau et al. |
| 2005/0059969 A1 | 3/2005 | McKinley |
| 2005/0065515 A1 | 3/2005 | Jahng |
| 2005/0065517 A1 | 3/2005 | Chin |
| 2005/0070917 A1 | 3/2005 | Justis |
| 2005/0080418 A1 | 4/2005 | Simonson et al. |
| 2005/0085813 A1 | 4/2005 | Spitler et al. |
| 2005/0090822 A1 | 4/2005 | DiPoto |
| 2005/0090833 A1 | 4/2005 | DiPoto |
| 2005/0113833 A1 | 5/2005 | Davison |
| 2005/0124991 A1 | 6/2005 | Jahng |
| 2005/0131407 A1 | 6/2005 | Sicvol et al. |
| 2005/0131408 A1 | 6/2005 | Sicvol et al. |
| 2005/0131421 A1 | 6/2005 | Anderson et al. |
| 2005/0131422 A1 | 6/2005 | Anderson et al. |
| 2005/0137461 A1 | 6/2005 | Marchek et al. |
| 2005/0137593 A1 | 6/2005 | Gray et al. |
| 2005/0149022 A1 | 7/2005 | Shaolian et al. |
| 2005/0149035 A1 | 7/2005 | Pimenta et al. |
| 2005/0154389 A1 | 7/2005 | Selover et al. |
| 2005/0171540 A1 | 8/2005 | Lim et al. |
| 2005/0182410 A1 | 8/2005 | Jackson |
| 2005/0192570 A1 | 9/2005 | Jackson |
| 2005/0245928 A1 | 11/2005 | Colleran et al. |
| 2005/0251139 A1 | 11/2005 | Roh |
| 2005/0277942 A1 | 12/2005 | Kullas et al. |
| 2006/0030839 A1 | 2/2006 | Park et al. |
| 2006/0036252 A1 | 2/2006 | Baynham et al. |
| 2006/0069391 A1 | 3/2006 | Jackson |
| 2006/0084980 A1 | 4/2006 | Melkent et al. |
| 2006/0111713 A1 | 5/2006 | Jackson |
| 2006/0111714 A1 | 5/2006 | Foley |
| 2006/0195114 A1 | 8/2006 | Bertagnoli |

(56) References Cited

U.S. PATENT DOCUMENTS

| | | | |
|---|---|---|---|
| 2006/0200135 A1 | 9/2006 | Sherman et al. | |
| 2006/0217735 A1 | 9/2006 | MacDonald et al. | |
| 2006/0247658 A1 | 11/2006 | Pond et al. | |
| 2006/0264934 A1 | 11/2006 | Fallin | |
| 2006/0264962 A1 | 11/2006 | Chin et al. | |
| 2006/0293680 A1 | 12/2006 | Jackson | |
| 2007/0043359 A1 | 2/2007 | Altarac et al. | |
| 2007/0213716 A1 | 9/2007 | Lenke et al. | |
| 2008/0077138 A1 | 3/2008 | Cohen et al. | |
| 2008/0077139 A1 | 3/2008 | Landry et al. | |
| 2008/0183214 A1 | 7/2008 | Copp et al. | |
| 2009/0099605 A1 | 4/2009 | Fallin et al. | |
| 2009/0149892 A1 | 6/2009 | Stad et al. | |
| 2009/0216327 A1 | 8/2009 | Miller et al. | |
| 2009/0216328 A1 | 8/2009 | Birkmeyer et al. | |
| 2009/0221877 A1 | 9/2009 | Woods | |
| 2009/0221879 A1 | 9/2009 | Gorek | |
| 2009/0228056 A1 | 9/2009 | Jackson | |
| 2009/0264893 A1 | 10/2009 | Beale et al. | |
| 2010/0004695 A1* | 1/2010 | Stad | A61B 17/708 606/86 A |
| 2010/0030289 A1 | 2/2010 | Casavant et al. | |
| 2010/0137915 A1 | 6/2010 | Anderson et al. | |
| 2010/0298647 A1 | 11/2010 | Black et al. | |
| 2010/0331901 A1 | 12/2010 | Iott et al. | |
| 2011/0015678 A1 | 1/2011 | Jackson | |
| 2011/0077692 A1 | 3/2011 | Jackson | |
| 2011/0137358 A1 | 6/2011 | Manninen | |
| 2011/0152940 A1 | 6/2011 | Frigg et al. | |
| 2011/0172494 A1 | 7/2011 | Bass et al. | |
| 2011/0238120 A1 | 9/2011 | Chin | |
| 2011/0245884 A9 | 10/2011 | Brumfield et al. | |
| 2012/0089191 A1 | 4/2012 | Altarac et al. | |
| 2012/0123477 A1 | 5/2012 | Landry et al. | |
| 2012/0158070 A1 | 6/2012 | Jackson | |
| 2012/0197302 A1 | 8/2012 | Fallin | |
| 2012/0226284 A1 | 9/2012 | Sorrenti et al. | |
| 2012/0303034 A1 | 11/2012 | Woolley et al. | |
| 2013/0066387 A1 | 3/2013 | Beger et al. | |
| 2013/0110113 A1 | 5/2013 | Glazer | |
| 2013/0184763 A1* | 7/2013 | McClintock | A61B 17/7079 606/279 |
| 2013/0245694 A1 | 9/2013 | Choi et al. | |
| 2014/0249591 A1* | 9/2014 | Peultier | A61B 17/7077 606/86 A |
| 2014/0277151 A1 | 9/2014 | Fowler et al. | |
| 2014/0277167 A1 | 9/2014 | Hutton et al. | |

FOREIGN PATENT DOCUMENTS

| | | |
|---|---|---|
| DE | 29710979 U1 | 8/1997 |
| DE | 19726754 A1 | 2/1999 |
| DE | 10027988 | 1/2002 |
| EP | 0528177 | 2/1993 |
| EP | 0528562 | 2/1993 |
| EP | 0611116 A1 | 8/1994 |
| EP | 0665731 A1 | 8/1995 |
| EP | 1006888 | 6/2000 |
| EP | 1027988 | 8/2000 |
| EP | 1248568 | 10/2002 |
| EP | 1374786 | 1/2004 |
| EP | 1468652 | 10/2004 |
| EP | 1545355 | 6/2005 |
| SU | 839513 A1 | 6/1981 |
| WO | 93/18722 | 9/1993 |
| WO | 9409726 A1 | 5/1994 |
| WO | 9514437 | 6/1995 |
| WO | 97/14457 | 4/1997 |
| WO | 9822030 A1 | 5/1998 |
| WO | 98/36785 | 8/1998 |
| WO | 98/38918 | 9/1998 |
| WO | 99/29242 | 6/1999 |
| WO | 99/51139 | 10/1999 |
| WO | 01/037744 | 5/2001 |
| WO | 0141681 A1 | 6/2001 |
| WO | 01/056479 | 8/2001 |
| WO | 01/060232 | 8/2001 |
| WO | 01/060234 | 8/2001 |
| WO | 01/060262 | 8/2001 |
| WO | 01/060270 | 8/2001 |
| WO | 2001060263 | 8/2001 |
| WO | 01/095823 | 12/2001 |
| WO | 02/085217 | 10/2002 |
| WO | 03020110 | 3/2003 |
| WO | 03028566 | 4/2003 |
| WO | 03/037170 | 5/2003 |
| WO | 03/057055 | 7/2003 |
| WO | 03/088810 | 10/2003 |
| WO | 03/088878 | 10/2003 |
| WO | 04004584 | 1/2004 |
| WO | 04017847 | 3/2004 |
| WO | 04021899 A1 | 3/2004 |
| WO | 04/028382 | 4/2004 |
| WO | 04037074 A2 | 5/2004 |
| WO | 04041100 A1 | 5/2004 |
| WO | 04080318 A1 | 9/2004 |
| WO | 05018466 A2 | 3/2005 |
| WO | 05023123 A1 | 3/2005 |
| WO | 05032358 | 4/2005 |
| WO | 05060534 A2 | 7/2005 |
| WO | 05072081 | 8/2005 |
| WO | 2006060430 A1 | 6/2006 |
| WO | 2006116662 A1 | 11/2006 |

OTHER PUBLICATIONS

Abram Reitblat et al., U.S. Appl. No. 61/783,098, filed Mar. 14, 2013.

Office Action from U.S. Appl. No. 11/526,785, dated Jan. 8, 2009.

Leu et al., Percutaneous Fusion of the Lumbar Spine, State of the Art Reviews, vol. 6, No. 3, pp. 593-604, Sep. 1992.

Kambin, Arthroscopic Lumbar Intervertebral Fusion, Chapter 95, The Adult Spine, vol. 2, pp. 2037-2046, Jan. 1997.

Bare Bones; Monthly Executive Summary, vol. 12, No. 1, p. 1-4, Jan. 2003.

Kambin et al., Anterior col. Support for Failed Fusion, Revision Spine Surgery, pp. 589-600, published Jan. 1999.

Kambin, The Role of Minimally Invasive Surgery in Spinal Disorders, Advance Operative Orthopedics, vol. 3, pp. 147-171, Dec. 1994.

Sofamor Danek; Metrx, X-Tube, Refraction System; Sofamor Danek Web page information p. 1-2, printed Mar. 29, 2005.

Kambin, "Arthroscopic Microdiscectomy", The Journal of Arthroscopy, vol. 8, No. 3, pp. 287-295, Sep. 1992.

Kambin et al, "Percutaneous Posterolateral Lumbar Discectomy and Decompression with a 6.9-millimeter cannula", The Journal of Bone and Joint Surgery, pp. 822-831, Jul. 1991.

Kambin, "Arthroscopic Microdiskectomy", The Mount Sinai Journal of Medicine, vol. 58, No. 2, Mar. 1991, pp. 159-164.

Kambin, "Posterolateral Percutaneous suction-excision of herniated lumbar intervertebral discs", Clinical Orthopaedics and Related Research. No. 207, pp. 37-42, Jun. 1988.

Diapason, Surgical Texchnique Catalog, Diapasan Spinal System, Jan. 2002.

Kambin, Posterolateral Percutaneous Lumbar Interbody Fusion, Arthroscopic Microdiscectomy, pp. 117-121, Jan. 1991.

Sofamor Danek; Sextant CD Horizon Sextant Rod Insertion System, Surgical Technique, Techniques, p. 1-29, 2003.

Kambin, Posterolateral Percutaneous Lumbar Discectomy and Decompression Arthroscopic Microdiscectomy, Section IV. pp. 67-100, Jan. 1991.

Smith and Nephew; 6.5mm and 4.0mm Cannulated Screws, Surgical Technique, p. 1-24, 1998.

Maxcess; XLIF 90° Surgical Technique. Nuvasive Creative Spine Technology Product Brochure, p. 1-26, 2005.

Pathfinder; Minimally Invasive Pedicle Fixation System. Spinal Concepts Product Brochure p. 1-4, May 2003.

(56) References Cited

OTHER PUBLICATIONS

Sofamor Danek; Eclipse CD Horizon Eclipse Implants and Instruments, Information from the Sofamor Danek Web page, p. 1-3, printed Mar. 29, 2005.
Spinal Concepts; Access Dilation Port, Spinal Concepts Web Page information 2 pages, 2004.
Encore Spine; Degenerative System, Encore Surgical Product Brochure, p. 1-6, Oct. 2002.
Kambin, Minimally Invasive Techniques in Spinal Surgery Current Practice, Neurosurgical Focus, wwwspineuniversecom, 16 pages, printed Aug. 24, 2005.
Office Action from U.S. Appl. No. 10/868,075, dated Sep. 18, 2008.
Nex-Link; Spinal Fixation System, Spinal Concepts Web Page information, 1 page, "(retrieved Mar. 25, 2005)".
Moss Miami Surgical Texhnique, DePuy, 14 pages, 1998.
T. Wade Fallin et al., U.S. Appl. No. 11/526,785, filed Sep. 25, 2006.
T. Wade Fallin et al., U.S. Appl. No. 12/316,637, filed Dec. 15, 2008.
T. Wade Fallin et al., U.S. Appl. No. 11/178,035, filed Jul. 8, 2005.
Jeffery Arnett et al., U.S. Appl. No. 11/904,029, filed Sep. 25, 2007.
Kingsley Richard Chin et al., U.S. Appl. No. 13/972,493, filed Aug. 21, 2013.
Kingsley Richard Chin et al., U.S. Appl. No. 13/973,462, filed Aug. 22, 2013.
T. Wade Fallin et al., U.S. Appl. No. 14/036,617, filed Sep. 25, 2013.
T. Wade Fallin et al., U.S. Appl. No. 14/036,634, filed Sep. 25, 2013.
Joshua A. Butters et al., U.S. Appl. No. 13/942,071, filed Jul. 15, 2013.
Abram Reitblat et al., U.S. Appl. No. 14/099,104, filed Dec. 6, 2013.
Abram Reitblat et al., U.S. Appl. No. 14/099,159, filed Dec. 6, 2013.
Abram Reitblat et al., U.S. Appl. No. 14/099,183, filed Dec. 6, 2013.

\* cited by examiner

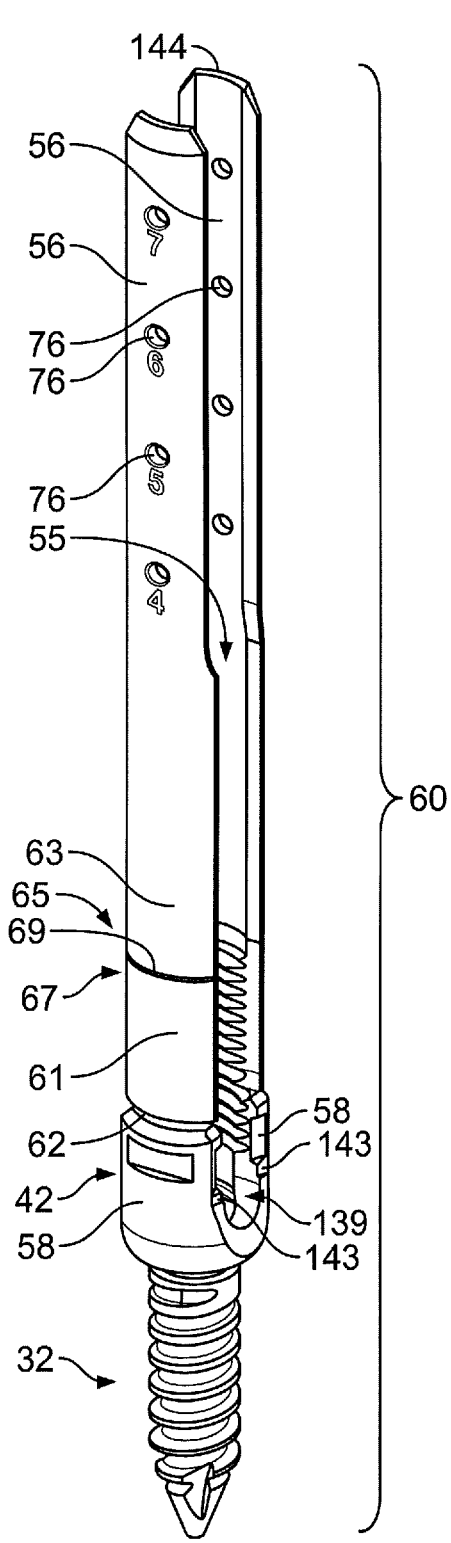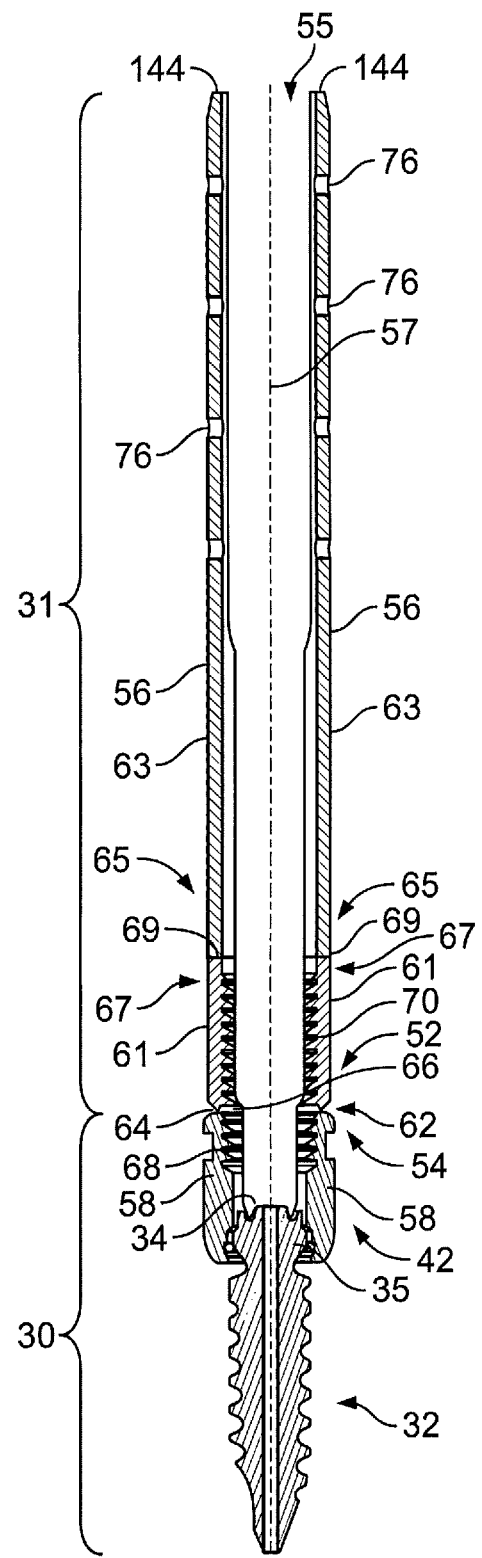
FIG. 2A
FIG. 2B

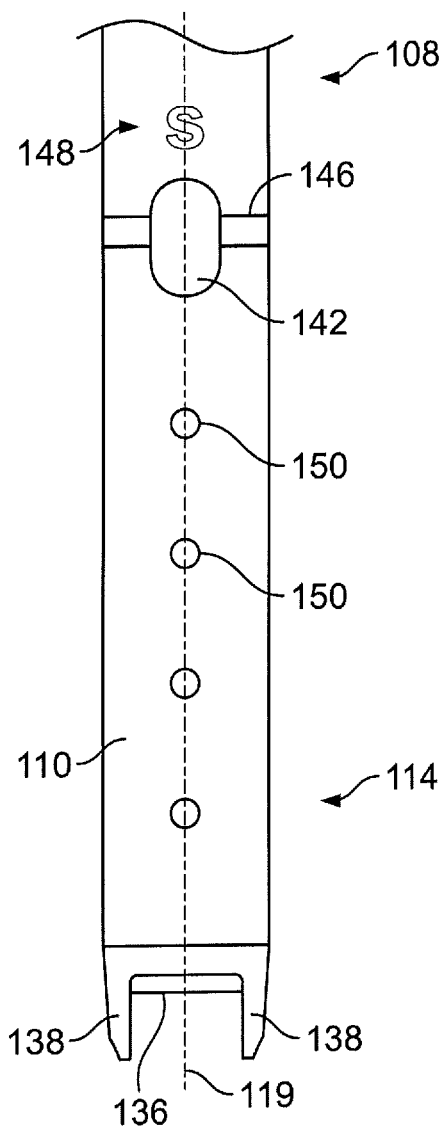
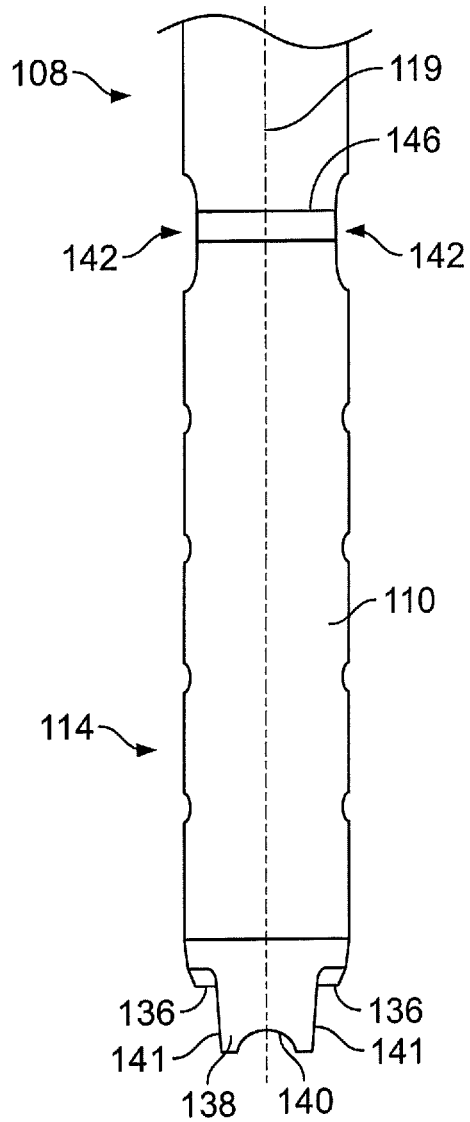
FIG. 8A
FIG. 8B

PERCUTANEOUS POSTERIOR SPINAL FUSION IMPLANT CONSTRUCTION AND METHOD

CROSS-REFERENCE TO RELATED APPLICATIONS

This application is a continuation of U.S. application Ser. No. 16/185,848, filed on Nov. 9, 2018, which is a continuation of U.S. application Ser. No. 14/099,104, filed on Dec. 6, 2013, the disclosures of which are incorporated herein by reference.

BACKGROUND OF THE INVENTION

The present invention relates to the percutaneous insertion of spinal fusion implants into the body of a patient and the affixation of those implants to the spine. In particular, the invention includes percutaneous posterior spinal fusion systems, devices used in conjunction with such systems, and associated methods.

Pedicle screw fixation constructs have been in use for decades in order to fuse adjacent vertebral segments to improve spinal stability or correct certain spinal deformities. Older approaches for inserting these fixation constructs involved open procedures, in which relatively large skin incisions were created to expose a substantial portion of the patient's spinal column, in order to allow for insertion of the pedicle screws and manipulation of spinal rods through openings adjacent to the heads of the screws.

Over time, less invasive approaches have been developed. Typically, in such approaches, pedicle screws are inserted into the pedicles of the same or adjacent vertebrae of a patient's spine through individual percutaneous incisions corresponding to the pedicle screws. Fixation or fusion rods are then inserted into the body through one of those incisions, or through an additional incision adjacent to the most cephalad or caudal pedicle screw, and the rod is rigidly connected to the pedicle screws such that the rod extends along the longitudinal axis of the spine (i.e., along the cephalad/caudal direction) in order to fix the relative positions of the adjacent vertebrae to which the rod is connected. In some such minimally invasive procedures, a device (e.g., a cannula, tower, or portal) is connected to each of the pedicle screws and extends through the respective percutaneous incision. Moreover, it is known to utilize separate elongate blades connected with the screws. Such devices provide a percutaneous passageway through the tissue from each incision to the respective pedicle screw, in order to aid in the insertion of a spinal rod. Examples of such passageway devices are described in commonly-assigned U.S. Pat. No. 7,955,355 ("the '355 Patent") and U.S. Pat. No. 8,002,798 ("the '798 Patent"), the entireties of which are hereby incorporated by reference herein as if fully set forth herein.

Although considerable effort has been devoted in the art to optimization of such minimally invasive systems, still further improvement would be desirable.

BRIEF SUMMARY OF THE INVENTION

One aspect of the present invention provides a system for manipulating portions of a spinal fusion system. The system according to this aspect of the invention desirably includes a connecting element, a passageway device, and a tubular member. The connecting element is preferably attachable to a vertebra of the spine, and a distal end of the passageway device is preferably connected to the connecting element. The tubular member preferably has an opening through its sidewall between its proximal and distal ends, and the tubular member is preferably removably positionable over the passageway device in an inserted position. In that position, an open interior portion of the tubular member preferably receives the passageway device within it.

According to another aspect of the invention, the tubular member may be structured such that, when it is positioned in the inserted position, its distal end is positioned proximate the connecting element and a feature of the passageway device is positioned adjacent to the opening. According to a further aspect of the invention, the feature may be the proximal end of the passageway device. According to yet another aspect of the invention, the sidewall of the tubular member may include a visible marking proximate the opening. In accordance with a further aspect of the invention, the visible marking may be indicative of a length of the passageway device. According to another aspect of the invention, the tubular member may include a second opening through its sidewall between the proximal and distal ends.

According to other aspects of the invention, the tubular member may be a counter torque tube having a handle projecting laterally therefrom. According to a further aspect of the invention, the distal end of the tubular member may be structured to engage the connecting element in the inserted position so as to prevent relative rotation between the connecting element and the tubular member.

According to another aspect of the invention, the system may further include a second connecting element, a second passageway device, and a second tubular member. The second connecting element is preferably attachable to a second vertebra of the spine, and a distal end of the second passageway device is preferably connected to the second connecting element. The second tubular member is desirably removably positionable over the second passageway device in a second inserted position. In that position, a second open interior portion of the tubular member preferably receives the second passageway device within it. The second tubular member may be movably connectable to the tubular member to allow for compression and distraction of the first and second vertebrae.

According to yet another aspect of the invention, the passageway device may include a first blade having a distal end connected to the connecting element, and the open interior portion of the tubular member may receive the first blade in the inserted position. In accordance with a further aspect of the invention, the open interior portion of the tubular member may include a first channel that receives the first blade when the tubular member is positioned in the inserted position. According to another aspect of the invention, the passageway device may include a second blade having a distal end connected to the connecting element, and the open interior portion of the tubular member may receive the second blade in the inserted position. In accordance with a further aspect of the invention, the open interior portion of the tubular member may include first and second channels that receive the respective first and second blades when the tubular member is positioned in the inserted position.

Another aspect of the present invention that provides a system for manipulating portions of a spinal fusion system desirably includes a connecting element attachable to a vertebra of the spine; a tubular member; and first and second blades, each of which has a distal end connected to the connecting element. The tubular member preferably has first and second channels formed therein that receive the respective first and second blades when the tubular member is positioned in an inserted position in which its distal end is proximate the connecting element.

According to yet another aspect of the invention, the system desirably further includes a second connecting element attachable to a second vertebra of the spine; a second tubular member; and third and fourth blades, each of which has a distal end connected to the second connecting element. The second tubular member preferably has third and fourth channels formed therein that receive the respective third and fourth blades when the second tubular member is positioned in a second inserted position in which its distal end is proximate the second connecting element.

According to other aspects of the invention, the tubular member may have an opening through its sidewall between proximal and distal ends of the tubular member. In accordance with a further aspect of the invention, the sidewall of the tubular member may include a visible marking proximate the opening.

Yet another aspect of the present invention that provides a system for manipulating portions of a spinal fusion system desirably includes a first shaft, a second shaft, and a manipulation device. The first and second shafts preferably have a respective first and second connector, and the distal ends of the first and second shafts are preferably connectable to respective first and second connecting elements affixed to respective first and second vertebrae of the spine. Desirably, the first connector is rotatable about the longitudinal axis of the first shaft. The manipulation device may be connectable to the first and second connectors and adapted to move the first and second shafts with respect to one another to induce relative movement between the first and second vertebrae.

According to one aspect of the invention, the second connector may be rotatable about the longitudinal axis of the second shaft. According to another aspect of the invention, the manipulation device may be a compressor adapted to move the first and second shafts towards one another. According to yet another aspect of the invention, the manipulation device may be a distractor adapted to move the first and second shafts away from one another. According to a further aspect of the invention, the first connector may be positioned in a middle portion of the first shaft between the proximal and distal ends of the first shaft. In accordance with another aspect of the invention, the proximal ends of the first and second shafts may be movably connectable to one another. In accordance with a further aspect of the invention, the proximal ends of the first and second shafts may be pivotably connectable together at a pivot point.

According to another aspect of the invention, the first shaft may have an open interior portion adapted to receive a passageway device extending proximally from the first connecting element. According to a further aspect of the invention, the passageway device may include a first blade having a distal end connected to the connecting element, and the open interior portion of the first shaft may include a first channel adapted to receive the first blade when the passageway device is received within the open interior portion. In accordance with another aspect of the invention, the first and second connecting elements may each include a respective anchoring element and coupling element, the anchoring element being affixable to a pedicle of a respective vertebra, and the coupling element being adapted to receive a spinal fusion element. In accordance with this aspect of the invention, the distal ends of the first and second shafts may be connectable to the respective first and second coupling elements.

Another aspect of the present invention that provides a system for manipulating portions of a spinal fusion system desirably includes a first shaft, a second shaft, and a manipulation device. The first and second shafts preferably have a respective first and second connector, and the distal ends of the first and second shafts are preferably connectable to respective first and second connecting elements affixed to respective first and second vertebrae of the spine. Desirably, the first and second connecting elements each have a passageway device extending proximally therefrom, and the first and second shafts desirably each have an open interior portion adapted to receive the respective passageway device therein when the distal end of the respective shaft is connected to the respective connecting element. The manipulation device may be connectable to the first and second connectors and adapted to move the first and second shafts with respect to one another to induce relative movement between the first and second vertebrae.

In accordance with other aspects of the invention, a first passageway device extending proximally from the first connecting element may include first and second blades each having a distal end connected to the first connecting element. In accordance with this aspect of the invention, the open interior portion of the first shaft may include a first and second channel adapted to receive the respective first and second blades when the first passageway device is received within the open interior portion of the first shaft. According to a further aspect of the invention, a second passageway device extending proximally from the second connecting element may include third and fourth blades each having a distal end connected to the second connecting element. In accordance with this aspect of the invention, the open interior portion of the second shaft may include a third and fourth channel adapted to receive the respective third and fourth blades when the second passageway device is received within the open interior portion of the second shaft.

Another aspect of the present invention provides a method of manipulating portions of a spinal fusion system. The method according to this aspect of the invention desirably includes: connecting a distal end of a first shaft to a first connecting element affixed to a first vertebra of a spine, the first shaft including a first connector; connecting a distal end of a second shaft to a second connecting element affixed to a second vertebra of the spine, the second shaft including a second connector; and manipulating a manipulation device connected to the first and second connectors so as to move the first and second shafts with respect to one another to induce relative movement between the first and second vertebrae. In accordance with this aspect of the invention, the first connector is preferably rotatable about the longitudinal axis of the first shaft.

In accordance with a further aspect of the invention, the first connector may rotate about the longitudinal axis of the first shaft during the step of manipulating the manipulation device. In accordance with another aspect of the invention, the second connector may be rotatable about a longitudinal axis of the second shaft. According to yet another aspect of the invention, the step of manipulating the manipulation device may include pivoting first and second arms of the manipulation device, each arm being connected to the respective first and second connector.

In accordance with another aspect of the invention, where the first vertebra may be located on a first side of the second vertebra, the method preferably further includes: disconnecting the distal end of the first shaft from the first connecting element; repositioning the first shaft on a second side of the second vertebra opposite the first side; and connecting the distal end of the first shaft to a connecting element affixed to a third vertebra located on the second side of the second vertebra. In accordance with a further aspect of the invention, the method may further include rotating the second connector of the second shaft towards the first shaft. In accordance with yet a further aspect of the invention, the method may further include connecting the manipulation device to the first and second connectors. According to a further aspect of the invention, the method may further include disconnecting a proximal end of the first shaft from a proximal end of the second shaft before the step of repositioning the first shaft on the second side of the second vertebra. According to yet a further aspect of the invention, the method may further include reconnecting the proximal end of the first shaft with the proximal end of the second shaft after the step of repositioning the first shaft on the second side of the second vertebra. In accordance with yet a further aspect of the invention, the step of disconnecting the proximal end of the first shaft from the proximal end of the second shaft may comprise uncoupling a receiver element at the proximal end of the second shaft from an engagement end at the proximal end of the first shaft, and the step of reconnecting the proximal end of the first shaft with the proximal end of the second shaft may include reorienting the receiver element and coupling the receiver element to the engagement end. According to yet a further aspect of the invention, the step of reorienting the receiver element may include rotating the receiver element from the first side of the second vertebra to the second side of the second vertebra.

According to another aspect of the invention, the first and second connectors may each be positioned in a middle portion of the respective first and second shafts between the proximal and distal ends of the respective shafts. According to yet another aspect of the invention, the method may further include receiving a first passageway device within the first shaft and receiving a second passageway device within the second shaft, which first and second passageway devices extend proximally from the respective first and second connecting elements. In accordance with yet another aspect of the invention, the method may further include connecting a proximal end of the first shaft to a proximal end of the second shaft. In accordance with a further aspect of the invention, the proximal ends of the first and second shafts may be connected such that, during the step of manipulating the manipulation device connected to the first and second connectors, the first and second shafts pivot about a pivot point proximate the proximal ends of the first and second shafts.

Another aspect of the present invention provides a method of constructing a monolithic blade-screw. The method according to this aspect of the invention desirably includes providing a connecting element including a screw coupled to a cage. The cage is preferably adapted to receive a spinal fusion rod in it, and the cage preferably has a reduction portion connected to it at a frangible portion. The method according to this aspect of the invention desirably also includes affixing a distal end of a blade extension to a proximal end of the reduction portion.

According to another aspect of the invention, the method may further include integrally forming the cage and the reduction portion from a single piece of material. According to a further aspect of the invention, the cage and the reduction portion may include threads therealong, and the blade extension may not be threaded. According to yet a further aspect of the invention, the threads may have a generally horizontal flank facing towards the screw. According to yet another aspect of the invention, the step of affixing the distal end of the blade extension to the proximal end of the reduction portion may include welding the distal end of the blade extension to the proximal end of the reduction portion. According to another aspect of the invention, the screw may be polyaxially coupled to the cage. In accordance with another aspect of the invention, the method may further include modifying the shape of a component forming the blade extension. According to further aspects of the invention, the step of modifying the shape of the component may occur either before or after the step of affixing the distal end of the blade extension to the proximal end of the reduction portion. According to yet another aspect of the invention, the step of modifying the shape of the component may be performed by wire-cut electrical discharge machining. In accordance with yet another aspect of the invention, the method may further include coupling the screw to the cage before the step of providing the connecting element.

Another aspect of the present invention provides a monolithic blade-screw. The blade-screw according to this aspect of the invention desirably includes a connecting element and a blade extension. The connecting element preferably includes a screw coupled to a cage. The cage may be adapted to receive a spinal fusion rod in it, and the cage may have a reduction portion connected to it at a frangible portion. Desirably, a distal end of the blade extension may be affixed to a proximal end of the reduction portion.

According to another aspect of the invention, the cage and the reduction portion may be integrally formed from a single piece of material. According to a further aspect of the invention, the cage and the reduction portion may include threads therealong, and the blade extension may not be threaded. According to yet a further aspect of the invention, the threads may have a generally horizontal flank facing towards the screw. According to yet another aspect of the invention, the distal end of the blade extension may be affixed to the proximal end of the reduction portion by a weld. In accordance with another aspect of the invention, the screw may be polyaxially coupled to the cage. In accordance with yet another aspect of the invention, a profile of the blade extension may vary between its proximal and distal ends.

BRIEF DESCRIPTION OF THE DRAWINGS

FIG. 2A is a perspective view of a blade-screw of FIG. 1.

FIG. 2B is a sectional view of the blade-screw of FIG. 2A.

FIGS. 8A-B are partial, elevational views of the counter torque tube of FIG. 7A.

DETAILED DESCRIPTION

Where reference is made herein to directional terms such as "proximal," "proximal most," "distal," and "distal most," it is to be understood that "proximal" and "proximal most" refer to locations closer to a user or operator of the device or method being described and that "distal" and "distal most" refer to locations further from a user or operator of the device or method being described.

Figure 1:
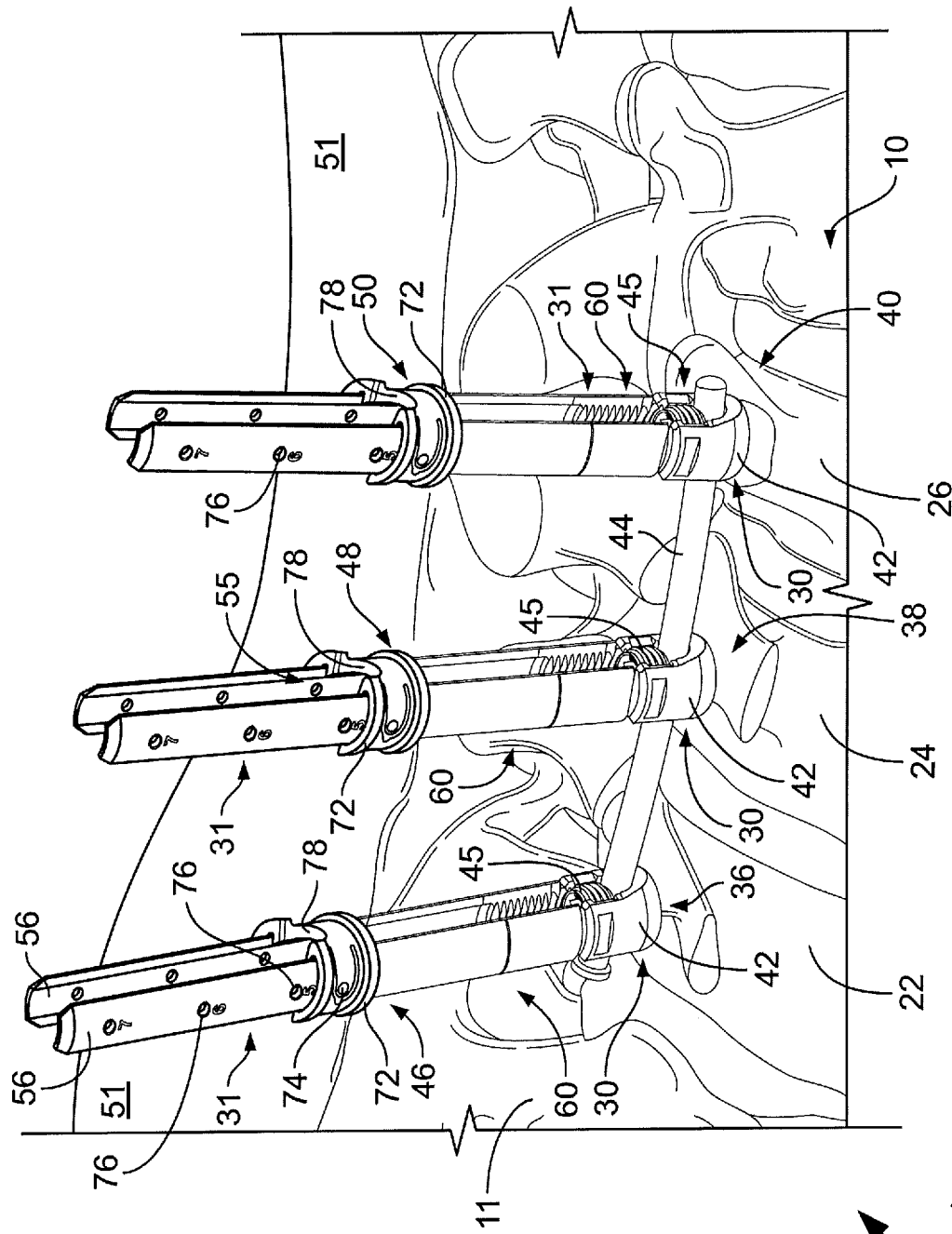
FIG. 1 is a perspective view of a system of blade-screws connected to a spine, in accordance with an embodiment of the present invention.

FIG. 1 illustrates a system of connecting elements 30, passageway devices 31, and a spinal fusion element or rod 44 connected to a spine 10. The spine 10 has a cephalad direction 12, a caudal direction 14, an anterior direction 16, a posterior direction 18, and a medial/lateral axis 20, all of which are oriented as shown by the arrows bearing the same reference numerals. In this application, "left" and "right" are used with reference to a posterior view, i.e., a view from behind the spine 10. "Medial" refers to a position or orientation toward a sagittal plane (i.e., plane of symmetry that separates left and right sides from each other) of the spine 10, and "lateral" refers to a position or orientation relatively further from the sagittal plane.

As shown in FIG. 1, the spine 10 includes a first vertebra 22, a second vertebra 24, and a third vertebra 26. The systems and methods herein may be applicable to any vertebra or vertebrae of the spine 10 and/or the sacrum 11. As such, the term "vertebrae" may be broadly interpreted to include all vertebrae, as well as the sacrum. As shown in the figure, the connecting elements 30 and associated passageway devices 31 are connected to respective pedicles 36, 38, 40 on the right side of the respective first, second, and third vertebrae 22, 24, 26. Although the system illustrated in FIG. 1 spans three vertebrae, other embodiments of systems in accordance with the present invention may span fewer or more vertebrae. For example, additional connecting elements 30 and passageway devices 31 may be connected to additional vertebrae along the spine 10.

The connecting elements 30 each include an anchoring element or screw 32 (see FIGS. 2A-B) implanted in the respective pedicles 36, 38, 40 and a coupling element or cage 42 for receiving the spinal fusion rod 44 therein. The cages 42 may be coupled to the respective screws 32 in various ways known in the art. For example, as shown in FIG. 2B, the cages 42 and the screws 32 may be polyaxially coupled. In other embodiments (not shown), the coupling between the cages 42 and the screws 32 may be a monoaxial coupling or a uniplanar coupling, or the cages 42 may be rigidly fixed to (e.g., integrally formed with) the screws 32. Each connecting element 30 may also include a set screw 45 for securing the rod 44 within the cage 42. The connecting elements 30 may have the same or similar structure as the connecting elements described in the '798 Patent. Alternatively, the connecting elements 30 may have the same or similar structure as the pedicle screws described in U.S. Pat. No. 7,988,713 ("the '713 Patent") or the pedicle screws, pedicle hooks, or lamina hooks described in U.S. Pat. No. 6,074,391 ("the '391 Patent"). The entire disclosures of the '713 Patent and the '391 Patent are hereby incorporated by reference herein as if fully set forth herein. Although the anchoring elements are illustrated herein as screws 32, it is to be understood that other types of anchoring elements capable of being secured to vertebral bone may be used, such as the above-referenced hooks described in the '391 Patent. Moreover, although the spinal fusion element 44 is illustrated herein as a rod 44, it is to be understood that other types of elements capable of securing together adjacent vertebrae may be used, such as plates, wires, rods, or articulating versions thereof.

The connecting elements 30 may be percutaneously inserted in the body in the same manner as described in the '798 Patent. That is, each of the connecting elements 30 may be inserted along a respective guide wire through a separate incision 46, 48, 50 in the skin 51. Sequential dilators may be used to enlarge the passageway between the incisions 46, 48, 50 and the respective pedicles 36, 38, 40. The screws 32 of the connecting elements 30 may be implanted in previously tapped bores in the associated pedicles, or the screws 32 may self-tap into the pedicles. The advancement of each screw 32 into a pedicle may be driven by a driver (not shown) having a distal end engaged with a driver interface 34 on the head 35 of the screw 32 (see FIG. 2B), such that a shaft of the driver extends proximally within the passageway device 31. The driver interface 34 of the head 35 may take the form of that disclosed in U.S. Pat. No. 8,231,635 ("the '635 Patent"), the entire disclosure of which is hereby incorporated by reference herein as if fully set forth herein, and the driver may take the form of any one of the screwdrivers disclosed in that patent. The driver may be a powered or a manually operated driver. Additionally, before the connecting elements 30 are inserted into the body, spinal navigation software and/or robotics may be used to help locate the appropriate pedicles 36, 38, 40 and to implant or help guide the implantation of the connecting elements 30 into the pedicles.

The passageway devices 31 are connected to the connecting elements 30 such that the passageway devices 31 extend proximally from the connecting elements 30 though the respective incisions 46, 48, 50. In particular, as shown in FIGS. 2A-B, the distal ends 52 of the passageway devices 31 are connected to the proximal ends 54 of the cages 42. The passageway devices 31 each provide a passageway 55 extending along an axis 57 from the incision 46, 48, 50 to the respective connecting element 30 to aid the percutaneous insertion of the rod 44. The axis 57 (and the associated passageway device 31) may be straight, as illustrated in the figures herein, or the passageway device 31 may define an angled or curved longitudinal axis, as disclosed in certain embodiments of U.S. patent application Ser. No. 14/034,021 ("the '021 Application"), filed on Sep. 23, 2013 and entitled "Lumbar-Sacral Screw Insertion and Manipulation," the entire disclosure of which is hereby incorporated by reference herein as if fully set forth herein. Each passageway device 31 may take the form of two blades 56 attached to opposing arms 58 of the associated cage 42. The blades 56 may be separately formed from and detachably connectible to the cages 42, as described in the '798 Patent. Alternatively, the blades 56 may be formed as a single piece with the associated cages 42, as also described in the '798 Patent. For example, FIGS. 1-2B illustrate an embodiment in which the blades 56 are integrally connected to the associated cages 42 to form monolithic blade-screws 60. In such an embodiment, the blades 56 may be connected to the cages 42 by frangible portions 62. Each frangible portion 62 may include a reduced thickness portion, which may be defined by grooves formed in either or both of the interior and exterior surfaces of the blade-screws 60 at the junction between the blades 56 and the respective arms 58 of the cages 42. In the embodiment illustrated in FIG. 2B, the frangible portions 62 are defined by a groove 64 along the exterior of the blade-screw 60 and a groove 66 along the interior of the blade-screw 60 that is aligned with the exterior groove 64. The frangible portions 62 provide a location for the blades 56 to be broken away from the cages 42 when desired.

The interior of each cage 42 may include threads 68 along the arms 58, and the passageway device 31 may include reduction threads 70 at least along the distal end 52 thereof. In other embodiments (not shown), the reduction threads 70 of the passageway device 31 may not be present while the threads 68 of the cage 42 are present. The set screw 45 (see FIG. 5A) is an externally threaded component structured to engage the reduction threads 70 of the passageway device 31 and the threads 68 of the cage 42. Both threads 68 and 70 are aligned such that the set screw 45 can be rotatably advanced distally along the reduction threads 70 of the passageway device 31, after which continued rotation of the set screw 45 will cause the set screw 45 to engage and advance along the threads 68 of the cage 42.

The threads 68 and/or the reduction threads 70 may have a tooth shape as disclosed in the '391 Patent. That is, as disclosed in the '391 Patent, and as illustrated in FIG. 2B herein, the flank of each thread facing in the distal direction (i.e., towards the screw 32) may be steep and, preferably, is generally horizontal, and the flank of each thread facing in the proximal direction (i.e., away from the screw 32) may be angled at about 30° with respect to the horizontal. The threads 106 of the set screw 45 are preferably complementary to the threads 68 and/or the reduction threads 70 (i.e., the steep flank of each thread 106 of the set screw 45 may be aligned oppositely to the steep flanks of the threads 68, 70).

As discussed above, the blades 56 of the passageway devices 31 are integrally connected to the cages 42 in the monolithic blade-screws 60. Such blade-screws 60 may be constructed by fabricating each cage 42 with its respective passageway device 31 as one piece. For example, a cage 42 with two blades 56 extending therefrom may be machined out of a single piece of material. In another example, the cage 42 with both blades 56 may be cast or molded as a unitary component. In other embodiments, however, subcomponents of the cage 42 and passageway device 31 may be formed separately and then integrally connected together, such as by welding. For example, the blades 56 and the cages 42 may be separately formed (e.g., by machining, casting, or molding), and the distal ends 52 of two blades 56 defining a passageway device 31 may be connected (e.g., by welding) to the proximal ends 54 of the arms 58 of a cage 42. In the case of welding, the welded regions may form the frangible portions 62. In yet another embodiment, each cage 42 may be integrally formed (e.g., by machining, casting, or molding) with two reduction portions 61 extending proximally from the proximal ends 54 of each of the arms 58 of the cage 42. The reduction portions 61 desirably include the reduction threads 70 of what will become the blades 56. Two blade extensions 63 may be separately formed, and the distal ends 65 of those extensions 63 may be integrally connected (e.g., welded) to the proximal ends 67 of the reduction portions 61 at connection 69. As shown in FIGS. 2A-B, each blade extension 63 may have a particular shape or profile that changes along its length. The final shape of the blade extensions 63 may be created when the separately formed blade extensions 63 are initially fabricated (e.g., machined, casted, or molded). Alternatively, the blade extensions 63 may initially be formed into larger pieces, which are then further refined to arrive at their final shape. For example, wire-cut electrical discharge machining ("EDM") may be used to modify the shape of the initially formed larger pieces in order to arrive at the final shape of the blade extensions 63. Such modifications (e.g., using wire-cut EDM) may be performed either before or after the blade extensions 63 are integrally connected to the reduction portions 61.

In some embodiments, the height of the cages 42 (i.e., the length along longitudinal axis 57) may be about 1.5 cm. The blades 56 may range between about 5 cm long and about 15 cm long. The reduction portions 61 may represent any portion of the length of the blades 56, e.g., about 1 cm to about 4 cm, but may preferably be about 2 cm in length. Systems in accordance with embodiments of the invention may include blade-screws 60 having blades 56 of different lengths, for example, because the distances to be traversed between the skin along a patient's back and the underlying pedicles may be different for different sized patients. For example, such systems may include blades 56 of two different lengths (i.e., long blades and short blades). In an exemplary embodiment, the long blades may be about 11 cm long, and the short blades may be about 7 cm long. Although the reduction portions 61 may represent any portion of that length, the reduction portions 61 may have the same length in both the long and short blades. For example, in an embodiment in which the reduction portions are about 2 cm, as discussed above, the blade extensions 64 of the short blades may be about 5 cm long and the blade extensions 64 of the long blades may be about 9 cm long.

Referring to FIG. 1, a coupling 72 may be connected to the blades 56 of each passageway device 31 along the length of the passageway device 31. The couplings 72 may take the form of those disclosed in U.S. Provisional Patent Application No. 61/783,098 ("the '098 Application"), filed on Mar. 14, 2013 and entitled "Systems and Methods for Percutaneous Spinal Fusion," the entire disclosure of which is hereby incorporated by reference herein as if fully set forth herein. In other embodiments, the coupling may take the form of the abutment members disclosed in the '798 Patent. In addition, the couplings 72 may be connected to the blades 56 in the same manner as disclosed in the '098 Application or the '798 Patent. For example, as disclosed in the '098 Application, the couplings 72 may include flexible tabs 74 having a boss or protuberance (not shown) extending inwardly therefrom for engaging holes 76 along the length of the blades 56. The couplings 72 may also include recesses 78 to provide an extracorporeal template for contouring or selecting the rod 44 to be implanted, as disclosed in the '098 Application. Such contouring or selection may also be done in the manner disclosed in commonly owned U.S. Pat. No. 8,177,817 ("the '817 Patent") or U.S. Patent Application Publication No. 2007/0233079 ("the '079 Publication"), the entireties of which are hereby incorporated by reference herein as if fully set forth herein.

Figure 3A:
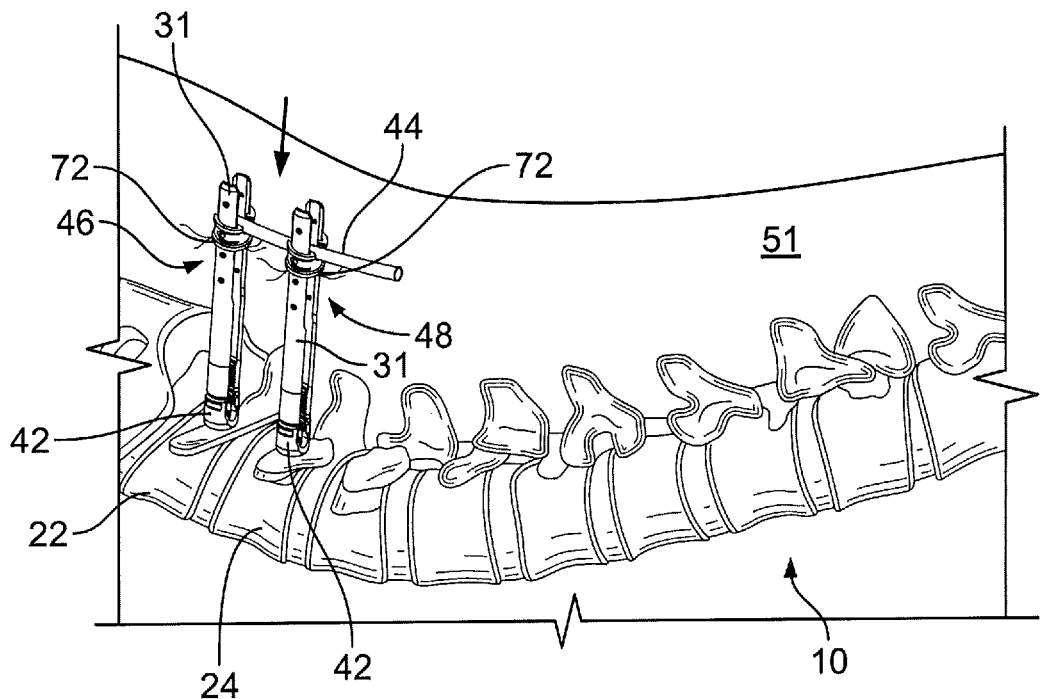
FIG. 3A is a perspective view of a system of blade-screws connected to a spine and being used for contouring a rod, in accordance with an embodiment of the present invention.
Figure 3B:
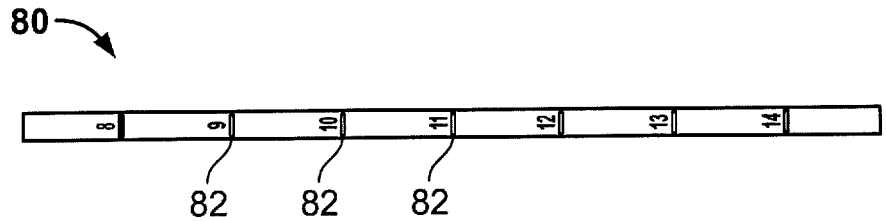
FIG. 3B is a plan view of a template rod, in accordance with an embodiment of the present invention.

Referring to FIG. 3A, a rod 44 is shown seated in the recesses 78 of the couplings 72 attached to two adjacent passageway devices 31. The rod 44 may be contoured (e.g., with a French bender or with an automated or robotic rod bending system in the operating room), selected from a kit of pre-shaped rods, or custom fabricated (e.g., by a CNC procedure) such that the rod 44 provides an optimal fit within the recesses 78, and thus, in turn, within the cages 42 of the connecting elements 30. Alternatively, a template rod 80, as shown in FIG. 3B, may be seated in the recesses 78 of the couplings 72. The template rod 80 may be similar in shape to rod 44 but may be easier to bend, particularly by hand, and may also include measurement markings 82 along its length. The template rod 80 may be bent and seated within the recesses 78, which steps may be repeated as necessary until the template rod 80 approximates the desired shape of the rod 44 to be implanted in the cages 42. The template rod 80 may then be used as a reference in contouring, selecting, or fabricating the rod 44 to be implanted.

Figure 4A:
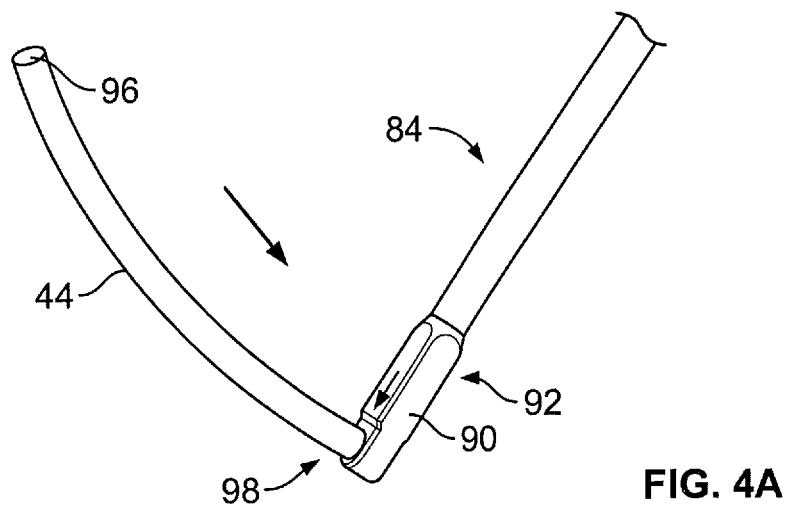
FIG. 4A is a partial, perspective view of a rod inserter and rod, in accordance with an embodiment of the present invention.

Once a rod 44 having the desired contour has been selected, it may be connected to a rod inserter 84, as shown in FIG. 4A. The rod inserter 84 is an elongate tool having a handle 86 (see FIGS. 4B-C) at its proximal end 88 and a connection structure 90 at its distal end 92 for detachably connecting to the rod 44. The proximal end 88 of the rod inserter 84 may also include an actuator 94 configured to operate the connection structure 90 so as to selectively secure and release the rod 44 to the connection structure 90. The rod 44 may be designed with a particular shape at one end for secure gripping by the connection structure 90 of the rod inserter 84. For example, the outer surface of the rod 44 at one end may have one or more flat sides (e.g., the rod may have a hexagonal cross-sectional profile at that end), and the interaction between the flat sides and the connection structure 90 may prevent rotation of the rod 44 about its longitudinal axis. The connection structure 90 may also be structured to securely grip the rod 44 while the rod 44 extends away at an angle to the rod inserter 84. For example, the rod 44 may extend at an approximately 90° angle to the rod inserter 84, as shown in FIG. 4A. In another embodiment, the rod 44 may extend at a 110° angle. In yet another embodiment, the connection structure 90 may be adjustable such that the angle of the rod 44 with respect to the rod inserter 84 can be varied.

Figure 4B:
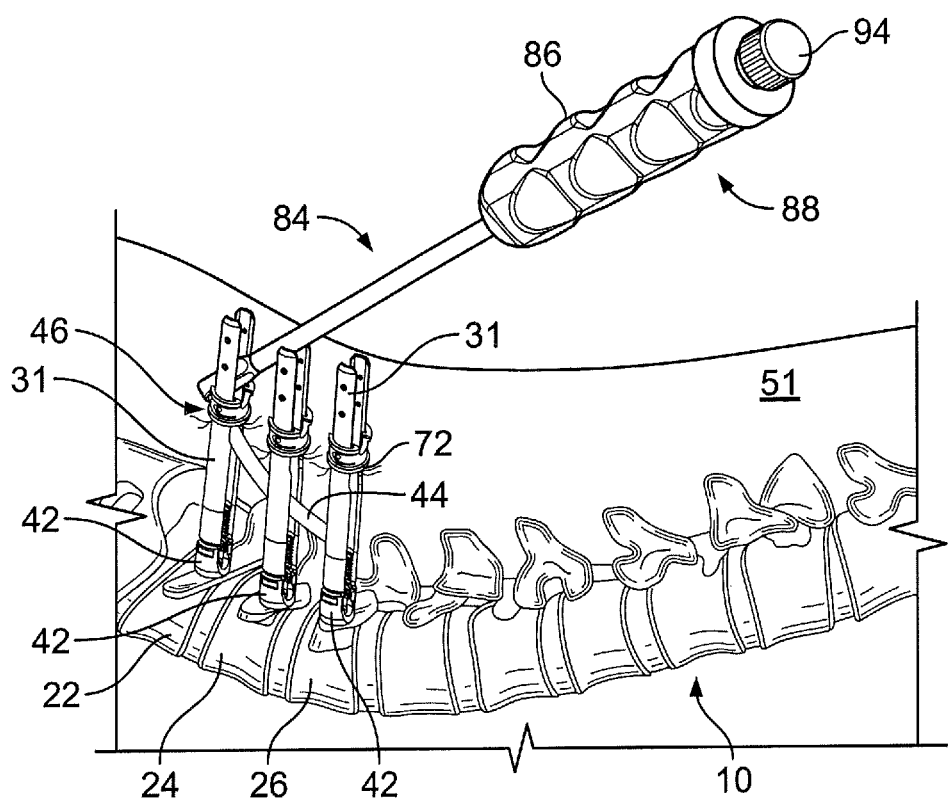
FIGS. 4B-C are perspective views of the rod inserter of FIG. 4A inserting the rod into a body through the system of blade-screws of FIG. 1.
Figure 4C:
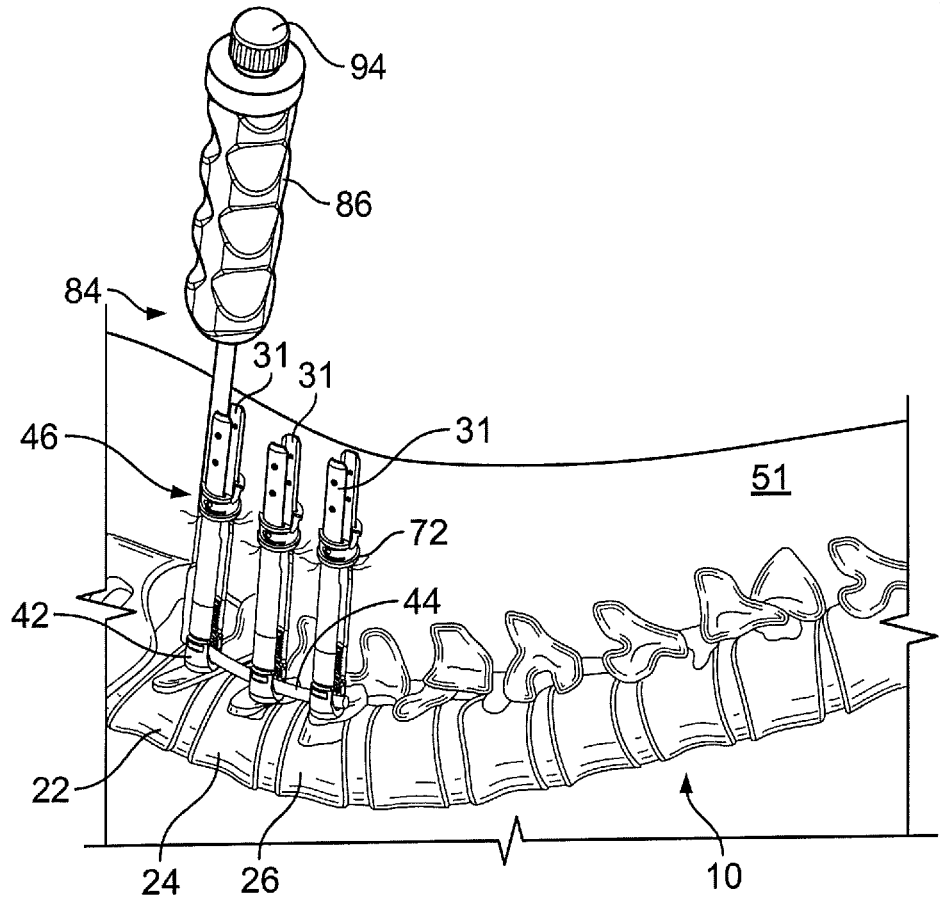

Once the rod 44 is attached to the rod inserter 84, the handle 86 of the rod inserter 84 may be grasped and used to manipulate the rod 44 into the body, as shown in FIGS. 4B-C, until the rod 44 extends between the cages 42 of the implanted connecting elements 30. For example, as shown in FIG. 4B, the far end 96 of the rod 44 opposite to the end 98 connected to the rod inserter 84 may be inserted through an incision 46 at one end of the system of blade-screws 60. That far end 96 of the rod 44 may then be passed subcutaneously across between the blades 56 of the passageway devices 31 until it is seated in the cage 42 of the connecting element 30 at the other end of the system of blade-screws 60. Then, as shown in FIG. 4C, the rod inserter 84 may be used to manipulate the end 98 of the rod 44 connected to the inserter 84 downwards until that end 98 is seated in the cage 42 of the connecting element 30 beneath the incision 46.

Figure 5A:
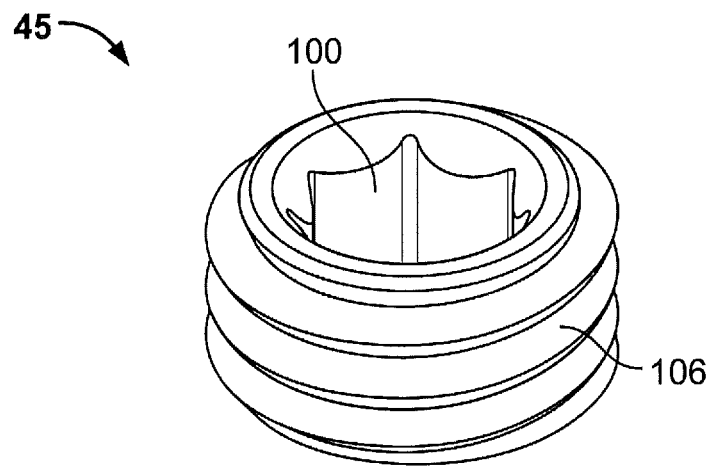
FIG. 5A is a perspective view of a set screw, in accordance with an embodiment of the present invention.
Figure 5B:
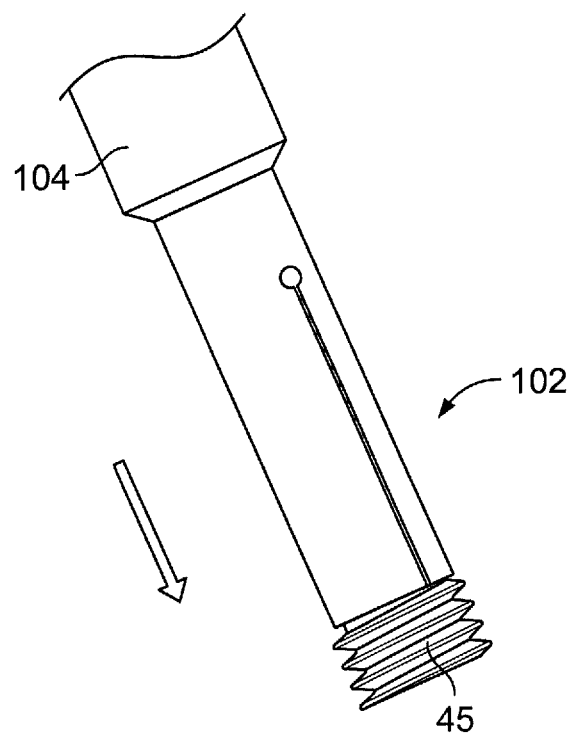
FIG. 5B is a partial, perspective view of the set screw of FIG. 5A engaged with a set screw driver, in accordance with an embodiment of the present invention.

Once the rod 44 is seated in the cages 42 of the connecting elements 30 attached to the vertebrae 22, 24, 26, a set screw 45, as shown in FIG. 5A, may be advanced into each of the cages 42. The set screw 45 includes a driving interface 100 engageable with the distal end 102 of a set screw driver 104, as shown in FIG. 5B, for advancing the set screw 45 along the passageway devices 31 and into the cages 42. The set screw 45 may include threads 106 along its outer surface for rotatably engaging the reduction threads 70 of the passageway devices 31 and the threads 68 of the cages 42.

Figure 6:
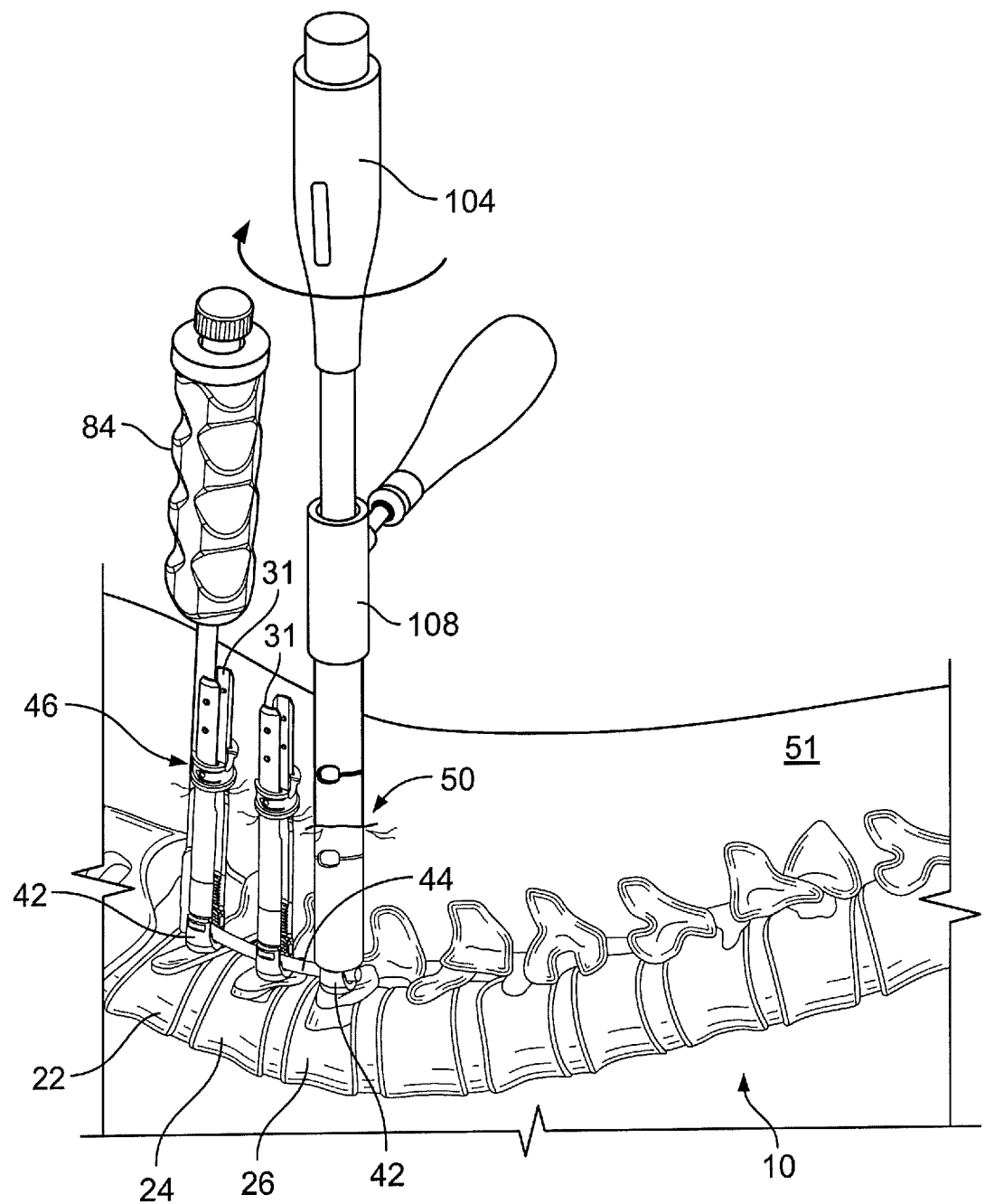
FIG. 6 is a perspective view of the system of blade-screws of FIG. 1, the rod inserter and rod of FIGS. 4A-C, the set screw driver of FIGS. 5B, and a counter torque tube, all being used together, in accordance with an embodiment of the present invention.

As shown in FIG. 6, the set screw driver 104 having a set screw 45 connected to its distal end is inserted distally through incision 50 and along the passageway device 31 extending through that incision 50. A counter torque tube 108 can be used in conjunction with the insertion and advancement of the set screw 45 with the set screw driver 104, as also shown in FIG. 6.

Figure 7B:
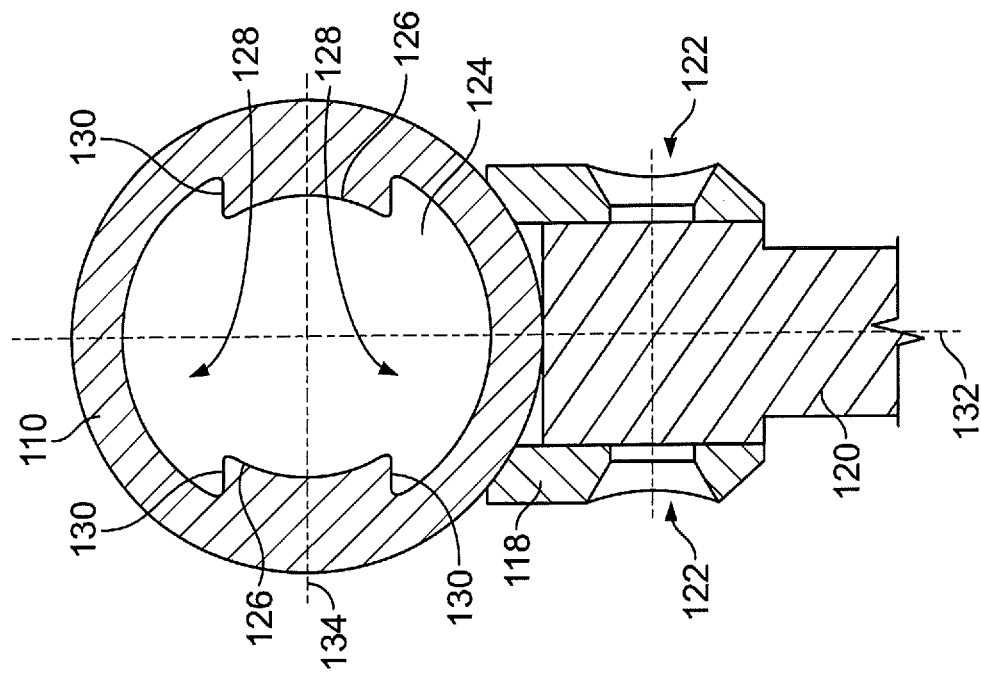
FIG. 7B is a partial, sectional view of the counter torque tube of FIG. 7A.
Figure 7A:
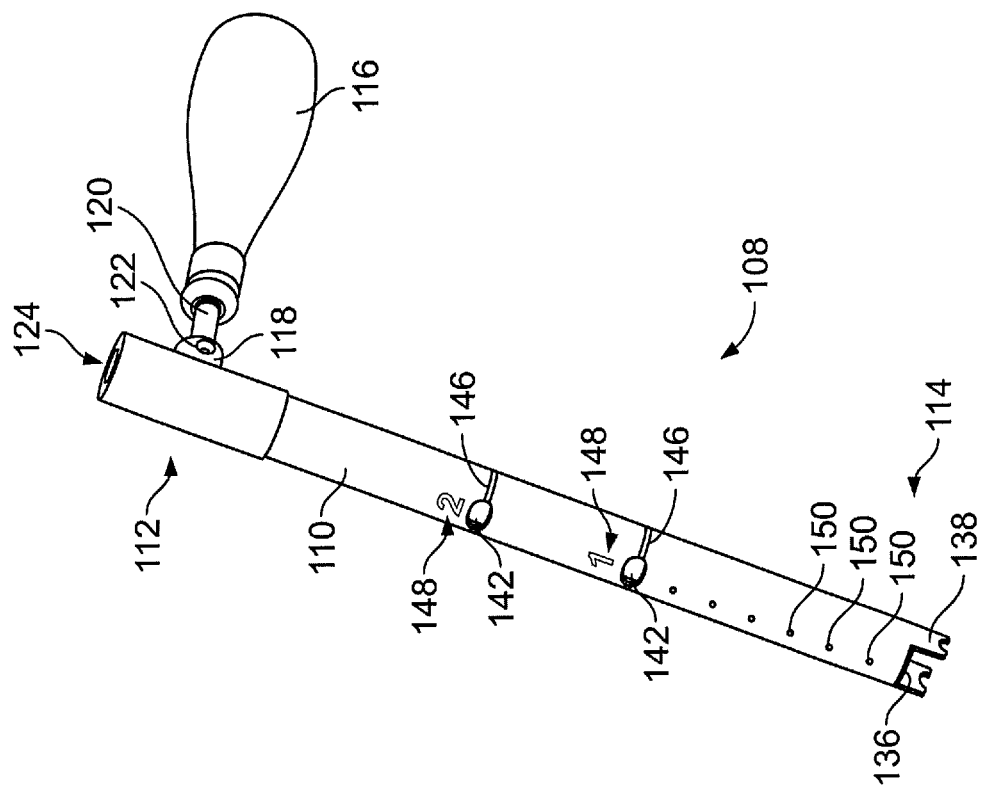
FIG. 7A is a perspective view of the counter torque tube of FIG. 6.

A perspective view of the counter torque tube 108 is shown in FIG. 7A. The counter torque tube 108 includes a tubular body 110 having a proximal end 112 and a distal end 114. A handle 116 is connected to the body 110 at the proximal end 112 by a connection member 118. The connection member 118 may be a substantially tubular structure projecting laterally from the proximal end 112 of the body 110, the tubular structure being configured to receive a stem 120 of the handle 116 therein. The stem 120 may be secured within the connection member 118 by one or more set screws (not shown) within one or more holes 122 in the connection member 118. When connected to the connection member 118, the handle 116 extends transverse to the longitudinal axis 119 of the body 110 and may extend substantially perpendicular to the longitudinal axis 119.

The tubular body 110 of the counter torque tube 108 has an open interior 124 designed to receive a passageway device 31 therein. A cross section of the counter torque tube 108 normal to the longitudinal axis 119 of the body 110 and taken along the axis of the handle 116 is shown in FIG. 7B. As shown in the figure, the interior surface 126 defining the open interior 124 includes opposing recessed grooves 128 or channels therein extending along the length of the body 110. The grooves 128 are structured to receive the blades 56 of the passageway device 31 when the counter torque tube 108 receives the passageway device 31 therein. As shown in FIG. 7B, the grooves 128 may have an arcuate shape along the plane normal to the longitudinal axis 119 of the body 110, which shape substantially matches the shape of the blades 56 in that plane. The grooves 128 include end surfaces 130 that constrain the blades 56 to remain in the grooves 128. As shown in FIG. 7B, the handle 116 preferably extends from the body 110 along an axis 132, which is perpendicular to an axis 134. When the counter torque tube 108 is advanced over one of the passageway devices 31 illustrated in FIGS. 1 and 6, and the blades 56 are received within the grooves 128, the axis 132 and the handle 116 desirably extends along the medial/lateral axis 20, and the axis 134 desirably extends along the cephalad and caudal directions 12, 14.

FIGS. 8A and 8B illustrate elevational views of a distal portion of the body 110 of the counter torque tube 108, taken along orthogonal directions. In particular, FIG. 8A is a view along axis 132, and FIG. 8B is a view along axis 134. As shown in the figures, the counter torque tube 108 may include a distal edge 136 arranged to abut the proximal end 54 of the cage 42 of the connecting element 30 when the body 110 of the counter torque tube 108 is fully advanced along the passageway device 31. In that regard, the cage 42 may be at least slightly wider than the passageway device 31 such that further distal movement of the counter torque tube 108 is prevented when the distal edge 136 of the body 110 comes into contact with the proximal end 54 of the cage 42. The distal edge 136 may be chamfered in order to ease bodily tissue aside during insertion of the counter torque tube 108. The counter torque tube 108 may also include opposing extensions 138 extending distally beyond the distal edge 136. At the distal ends of each of the extensions 138 is an arcuate cut-out 140 shaped to abut the rod 44. The length of each extension 138 may be dimensioned such that, when the counter torque tube 108 is fully advanced against the cage 42 of a connecting element 30, the contact between the cut-outs 140 and the rod 44 force the rod 44 to be fully seated within the cage 42. When the counter torque tube 108 is fully advanced, each of the extensions 138 is preferably positioned along a respective opening 139 (see FIG. 2A) defined between the arms 58 of the cage 42. Moreover, the width of each extension 138 may be dimensioned such that the opposite edges 141 of each extension 138 engage the respective edges 143 of the arms 58 along each opening 139. In that way, the engagement between the edges 141 of the extensions 138 and the edges 143 of the arms 58 of the cage 42 desirably constrains the rotational orientation of the cage 42 with respect to the body 110 of the counter torque tube 108 about the longitudinal axis 119. Alternatively, or in addition, the engagement between the blades 56 of the passageway device 31 and the grooves 128 of the counter torque tube body 110 desirably provides a similar constraint in the rotational orientation of the blade-screw 60 with respect to the body 110 of the counter torque tube 108.

One or more windows 142 may be positioned on the counter torque tube body 110 in alignment with the grooves 128 in the interior surface 126 of the body 110. The windows 142 are positioned such that the proximal edges 144 of the blades 56 (see FIGS. 2A-B) are visible through one or more of the windows 142 when the counter torque tube 108 is fully advanced against the connecting element 30. One or more laser markings, such as a line 146 bisecting the windows 142, may also be located on the counter torque tube body 110, such that the lines 146 are aligned with the proximal edges 144 of the blades 56 when the counter torque tube 108 is fully advanced against the connecting element 30. Multiple windows 142 (with or without corresponding lines 146) may be spaced apart along the longitudinal axis 119 of the body, and, as shown in FIG. 8B, one or more of those windows 142 may have an opposing window 142 located across the longitudinal axis 119 of the body. The locations of the various windows 142 and lines 146 along the longitudinal axis 119 of the body 110 desirably correspond to the different lengths of blades 56 provided with systems in accordance with some embodiments of the invention. As discussed above, different length blades 56, or blade-screws 60 having blades 56 of different lengths, may be provided with such systems to accommodate different distances to be traversed for different sized patients. Reference markings 148 may be positioned near each window 142 and/or line 146 to indicate which blade 56 length is associated with that window 142 and/or line 146.

The counter torque tube 108 may also include one or more holes 150 along at least a portion of the length of the body 110, preferably in alignment with the grooves 128 in the interior surface 126. Such holes 150 may be sized and positioned such that any fluid (bodily or otherwise) and/or tissue that may have become trapped between the blades 56 and the body 110 of the counter torque tube 108 (e.g., during insertion of the counter torque tube 108) may be released through the holes 150.

Returning to FIG. 6, the counter torque tube 108 may be advanced over one of the passageway devices 31, as shown in that figure. The counter torque tube 108 may be used in different ways. For example, when advancing the set screw 45 into engagement with the threads 70 of the blades 56 using the set screw driver 104, positioning the body 110 of the counter torque tube 108 around the passageway device 31 may help to align the set screw driver 104 along the longitudinal axis 57 of the blade-screw 60, and thus help prevent cross-threading of the set screw 45. In some embodiments, the coupling 72 may need to be removed from the blades 56 in order to allow the counter torque tube 108 to advance along the passageway device 31. In such cases, without the stability provided to the blades 56 by the coupling 72, the blades 56 may tend to pivot or flex slightly inwardly towards one another under pressure from the surrounding tissue. The grooves 128 in the counter torque tube body 110, along with their end surfaces 130, however, preferably constrain the desired positions of the blades 56 and provide stability to the blades 56 when the counter torque tube 108 is advanced along the passageway device 31. That stability provided by the counter torque tube 108 desirably protects portions of the blade-screw 60, such as the frangible portions 62 and the connections 69 between the blade extensions 63 and the reduction portions 61, by preventing the blades 56 from becoming prematurely disconnected from the connecting element 30 and by preventing the blade extensions 63 from becoming separated from the reduction portions 61. If the blades 56 pivot or flex slightly inwardly upon removing the coupling 72, the set screw driver 104 may be advanced together with the counter torque tube 108 such that the set screw driver 108 is positioned within the open interior 124 of the counter torque tube body 110 and such that the distal end of the set screw driver 104 (with or without the set screw 45 connected to it) projects distally from the distal end 114 of the body 110. Beneficially, in this arrangement, the set screw driver 104 (and the set screw 45, if connected to it) will first pass between the proximal edges 144 of the blades 56 and will help to keep the proximal edges 144 apart when they are engaged by the distal end 114 of the counter torque tube body 110 and guided into the grooves 128. If the proximal edges 144 of the blades 56 are not kept apart, the blades 56 might not properly be guided into the grooves 128.

If, after being inserted in the body, the rod 44 is not fully seated in one or more of the cages 42 (e.g., the rod 44 is slightly proud), the rod 44 can be further directed into a particular cage 42 in various ways. For example, the set screw 45 and set screw driver 104 can be used to advance the rod 44 towards the cage 42. In one example, the set screw driver 104 having a set screw 45 connected to its distal end can be advanced within the passageway device 31 until the set screw 45 engages the rod 44 and pushes it distally. If the rod 44 is located proximally of the reduction threads 70, the set screw driver 104 can be used to push the rod 44 distally until the set screw 45 contacts the reduction threads 70. The rod 44 can then be further advanced towards the cage 42 by rotating the set screw driver 104 to advance the set screw 45 along the reduction threads 70, which will further push the rod 44 towards the cage 42. Continued rotation of the set screw 45 will cause the set screw 45 to engage and advance along the threads 68 of the cage 42 until the rod 44 is fully seated within the cage.

In another example, the counter torque tube 108 can be used to push the rod 44 towards the cage 42 by advancing the body 110 of the counter torque tube 108 distally along a passageway device 31 until the cut-outs 140 at the distal end 114 of the body 110 engage the rod 44 and push it distally. The counter torque tube 108 can be used in this manner to advance the rod 44 for all or part of the distance to the cage 42. For example, the counter torque tube 108 can be used to advance the rod 44 until the rod is within the region of the passageway device 31 having the reduction threads 70, after which the set screw 45 and set screw driver 104 can be used to reduce the rod 44 the remaining distance into the cage 42, as discussed above.

During the advancement of the set screw 45 along the reduction threads 70 and/or the threads 68 of the cage 42, the body 110 of the counter torque tube 108 is desirably received around at least a portion of the passageway device 31. Preferably, the distal end 114 of the tube body 110 is positioned close to the set screw 45, and, more preferably, the distal end 114 is advanced distally along the passageway device 31 while the set screw 45 is advanced. By positioning the counter torque tube body 110 around the passageway device 31, the body 110 preferably constrains the blades 56 of the passageway device 31 to prevent the blades 56 from splaying outwardly during the threaded advancement of the set screw 45. Moreover, by positioning the counter torque tube 110 body near or in contact with the cage 42, the body 110 preferably constrains the arms 58 of the cage 42 to prevent the arms 58 from splaying outwardly during the threaded advancement of the set screw 45.

During final tightening of the set screw 45 against the rod 44 within the cage 42, the counter torque tube 108 is desirably fully advanced against the cage 42. The full and proper advancement of the counter torque tube 108 can be checked by confirming that a proximal edge 144 of one of the blades 56 of the passageway device 31 is aligned with the appropriate window 142 of the counter torque tube body 110, and, in some embodiments, is aligned with the appropriate laser marking or line 146. With the counter torque tube 108 fully advanced against the cage 42, the counter torque tube 108 desirably constrains the rotational orientation of the cage 42 and/or the blades 56 of the passageway device 31, as discussed above. Therefore, during final tightening of the set screw 45, the surgeon or other user preferably firmly holds the handle 116 of the counter torque tube 108 and/or provides any necessary torque to the handle 116 in the direction opposite to the direction of rotation of the set screw 45. This will desirably prevent the torque being applied to the set screw 45 by the set screw driver 104 from being transmitted to the associated vertebra of the spine 10 via the connecting element 30, or at least reduce the amount of torque that is transmitted to the spine.

The final tightening of the set screw 45 in the cage 42 may be performed by the set screw driver 104, or the final tightening may be performed by a torque wrench (not shown). The torque wrench may have a similar structure to the set screw driver 104, except that it may be constructed such that the torque applied by the torque wrench to the set screw 45 is limited to a pre-selected amount (e.g., 8 Nm (newton-meters)). Once a set screw 45 is finally tightened in one of the cages 42, as described above, the other cages 42 may be secured to the rod 44 by set screws 45 in the same manner. Preferably, after the rod 44 is secured within at least one of the cages 42 by a set screw 45, the rod inserter 84 may be disconnected from the rod 44 and removed from the body.

Before final tightening of the set screw 45 in the cage 42, the relative positions of the vertebrae may be adjusted. For example, while the rod 44 is positioned within the cages 42 but before the set screw 45 is tightened to the point that the cages 42 are locked with respect to the rod 44, two or more vertebrae may be moved in the cephalad and caudal directions 12, 14 towards one another (i.e., compression) and/or away from one another (i.e., distraction). One system and method for performing such compression and distraction is disclosed in U.S. Pat. No. 8,157,809 ("the '809 Patent"), the entire disclosure of which is hereby incorporated by reference herein as if fully set forth herein. Another similar system is illustrated in FIGS. 9A-13B and is discussed herein.

Figure 9A:
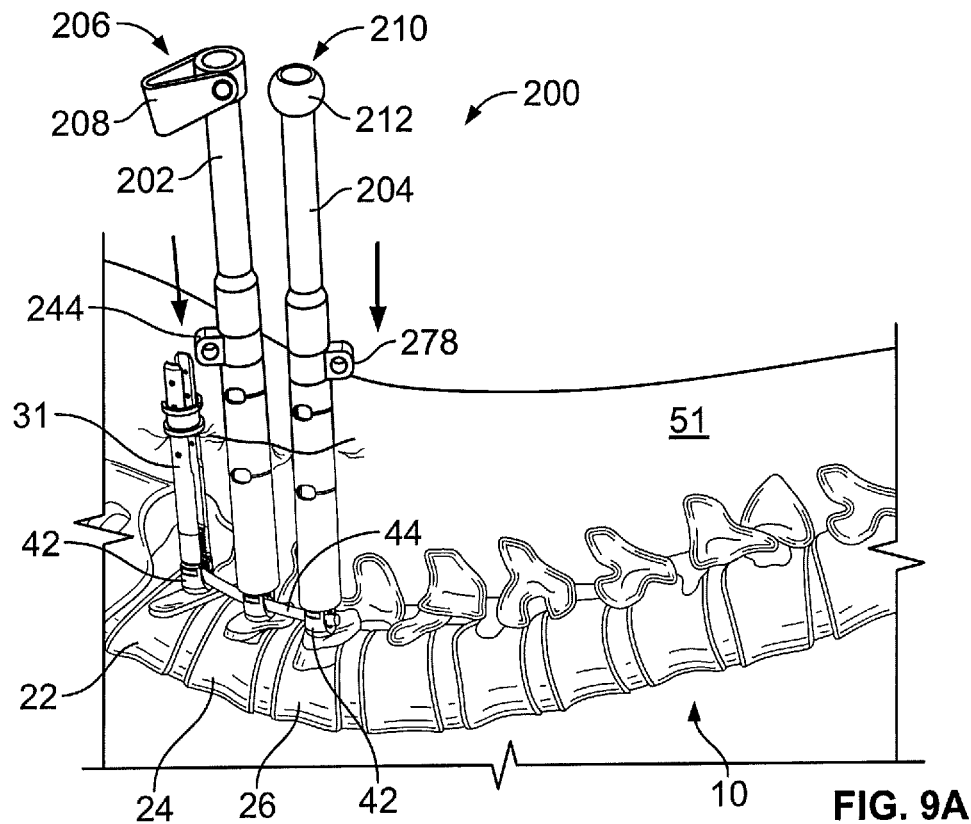
FIG. 9A is a perspective view of the system of blade-screws of FIG. 1 being used with components of a compression and distraction system in one configuration, in accordance with an embodiment of the present invention.
Figure 9B:
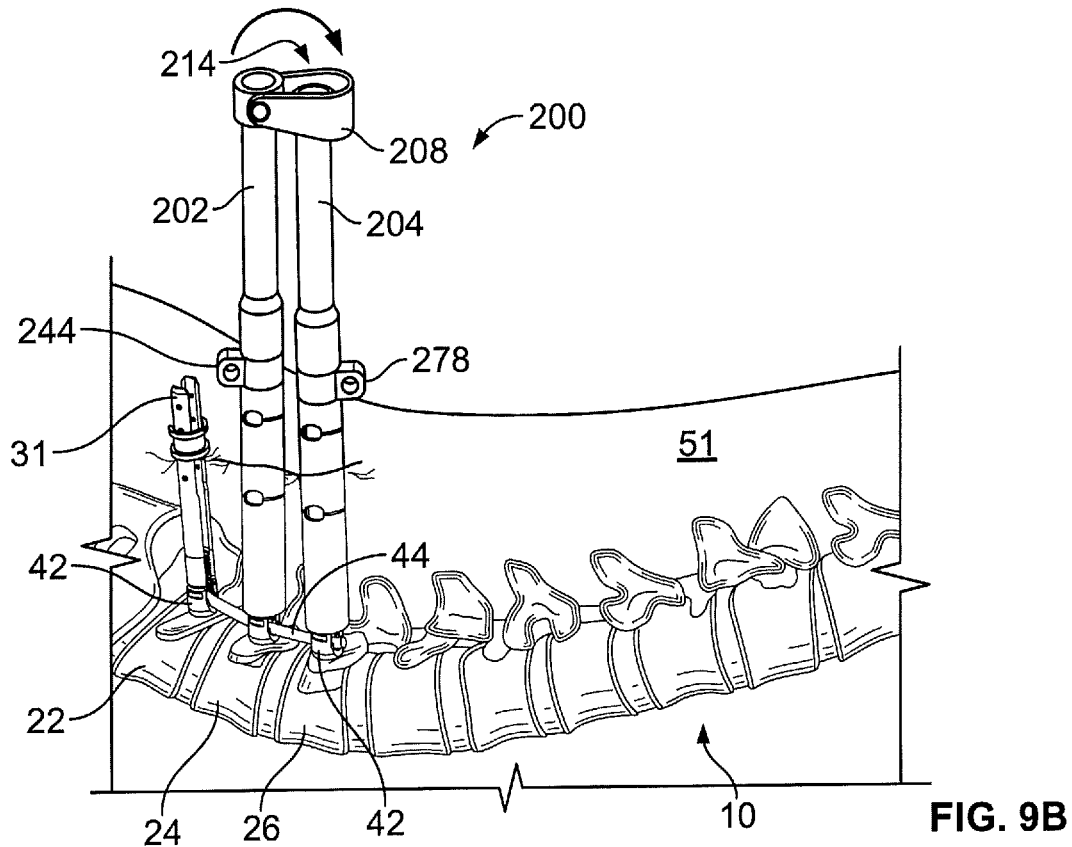
FIG. 9B is a perspective view of the system of blade-screws of FIG. 1 being used with the components of the compression and distraction system of FIG. 9A in another configuration, in accordance with an embodiment of the present invention.

FIGS. 9A-B illustrate a hinge shaft 202 and a ball shaft 204 of a compression and distraction system 200. As shown in those figures, the hinge shaft 202 and the ball shaft 204 have been inserted into the patient's body over and along a respective one of the passageway devices 31. Similar to the compression and distraction assembly disclosed in the '809 Patent, the proximal end 206 of the hinge shaft 202 includes a fulcrum or hinge 208, and the proximal end 210 of the ball shaft 204 includes a ball 212. The hinge 208 can receive the ball 212 therein, as illustrated in FIG. 9B, and the hinge 208 can be rotated about the proximal end 206 of the hinge shaft 202 from the position illustrated in FIG. 9A to the position illustrated in FIG. 9B in order to receive the ball 212. Once the ball 212 is received within the hinge 208 in the manner shown in FIG. 9B, a polyaxial fulcrum 214 is formed between the proximal ends 206, 210 of the shafts 202, 204 similar to that disclosed in the '809 Patent. Like the polyaxial fulcrum of the '809 Patent, the polyaxial fulcrum 214 desirably allows all rotational degrees of freedom such that the fulcrum 214 does not impart ancillary stresses or motion to the vertebrae during compression or distraction.

Figure 10A:
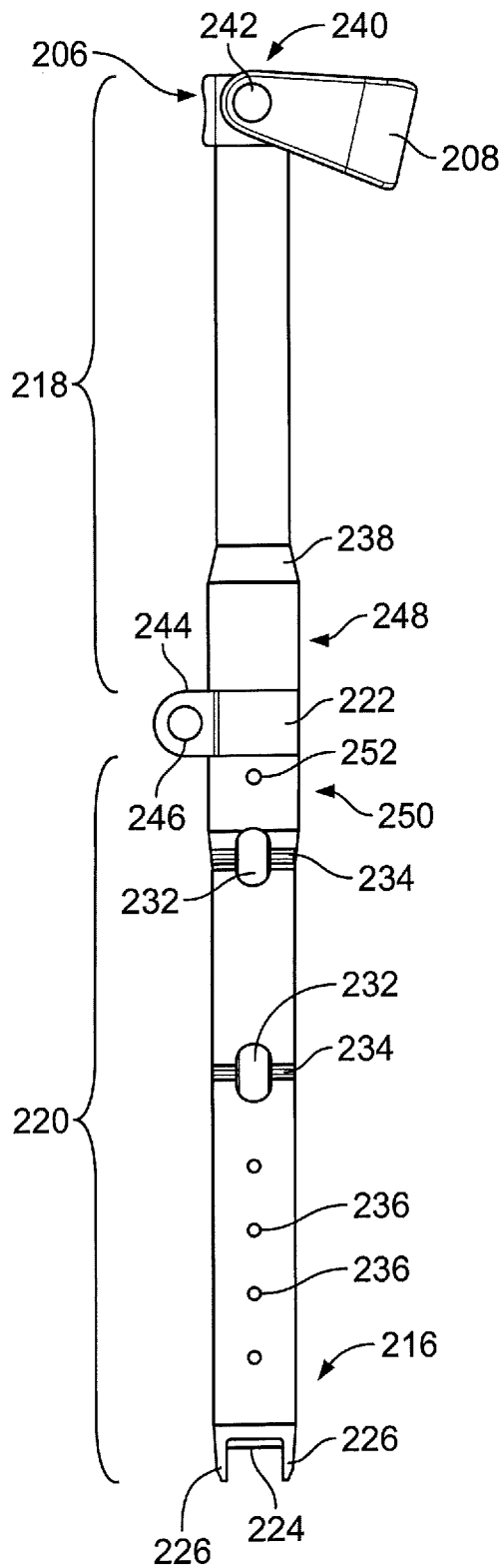
FIGS. 10A-B are elevational views of a hinge shaft of the compression and distraction system of FIGS. 9A-B.
Figure 10B:
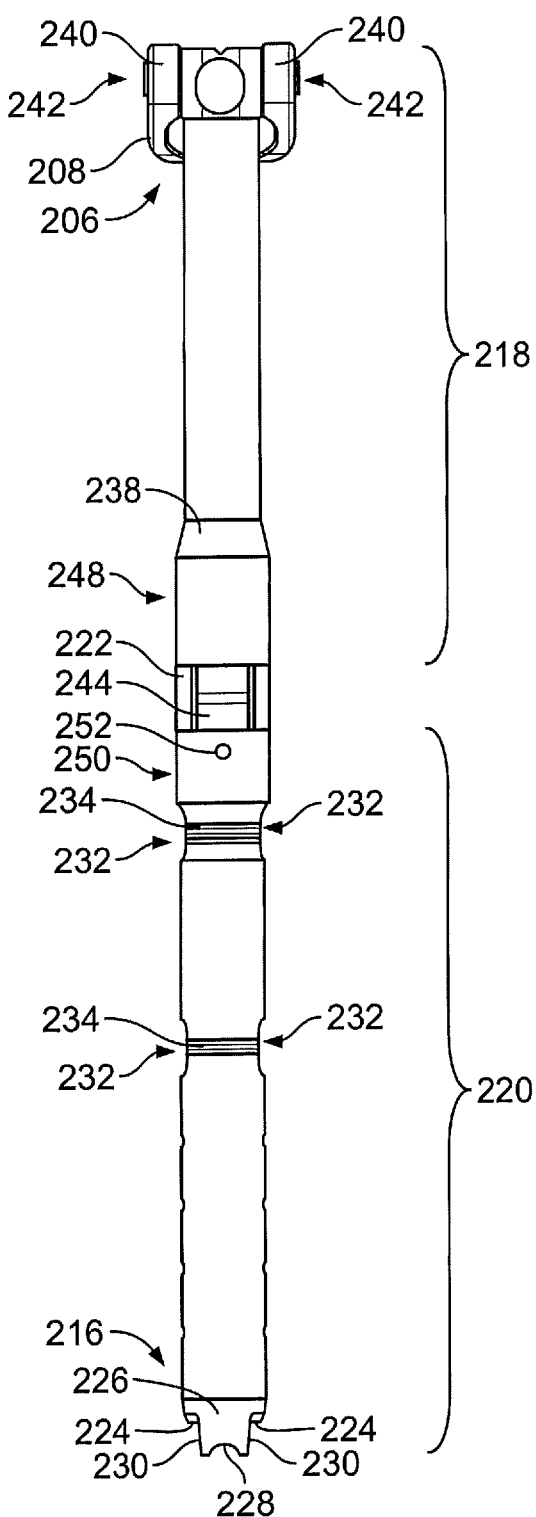

FIGS. 10A-B illustrate elevational views of the hinge shaft 202, taken along orthogonal directions. The hinge shaft 202 has a proximal end 206 and a distal end 216, with the hinge 208 being at the proximal end 206. The hinge shaft 202 includes a proximal shaft 218 and a distal shaft 220, with an eyelet ring 222 disposed therebetween. The distal shaft 220 may have a similar structure to the body 110 of the counter torque tube 108. That is, the distal shaft 220 desirably has a tubular shape with an open interior designed to receive a passageway device 31 therein. The open interior may have the same grooved structure as the counter torque tube 108, in order to similarly receive and constrain the blades 56 of the passageway device 31. The distal end 216 may also have the same structure for engaging the cage 42 of a connecting element 30 as the distal end 114 of the counter torque tube body 110. That is, the distal end 216 may have a chamfered distal edge 224 arranged to abut the proximal end 54 of the cage 42 of the connecting element 30 when the hinge shaft 202 is fully advanced against the cage 42. The distal end 216 may also include opposing extensions 226 with a cut out 228 shaped to abut the rod 44 and/or edges 230 for engaging the respective edges 143 of the arms 58 of the cage 42. Also, the distal shaft 220 may include one or more windows 232 and one or more laser markings, such as lines 234, arranged in the same manner as that described above with respect to the counter torque tube 108, such that the full and proper advancement of the hinge shaft 202 can be determined based on alignment with the proximal edges 144 of the blades 56. The distal shaft 220 may also include one or more holes 236 along at least a portion of the length of the distal shaft 220, preferably in alignment with the grooves in its interior surface. Such holes 236 are desirably sized and positioned in the same manner as the holes 150 in the counter torque tube 108, in order to similarly release any trapped fluid and/or tissue.

The proximal shaft 218 of the hinge shaft 202 may be narrower along at least a portion of its length, in order to reduce weight and material, and thus proximal shaft 218 may include a tapered portion 238. The hinge 208 is a generally U-shaped component sized to fit the proximal end 206 of the hinge shaft 202 between its ends 240. Each end 204 of the hinge 208 is connected to the proximal end 206 by a respective pin 242 such that the hinge 208 may rotate from one side to the other (as shown in FIGS. 9A-B) about the pins 242. The proximal shaft 218 preferably includes a passageway along its length that is open at each end of the proximal shaft 218 and that communicates with the open interior of the distal shaft 220. In that way, a tool, such as the set screw driver 104, can be passed down within the hinge shaft 202 through the open proximal end 206 in order to lock the position of the connecting element 30 with respect to the rod 44 by tightening the set screw 45.

An eyelet ring 222 is located between the proximal shaft 218 and the distal shaft 220. The eyelet ring 222 includes a laterally extending tab 244 having a bore 246 formed within it. The bore 246 is configured to receive a portion of one or more compression or distraction tools, as discussed below. Although the bore 246 may have an hourglass shape along its central axis, as disclosed in the '809 Patent, the bore 246 may alternatively have another shape, such as a substantially cylindrical shape along its central axis. The eyelet ring 222 is rotatable about the longitudinal axis of the hinge shaft 202, such that the angular position of the tab 244 around the hinge shaft 202 can be varied. The hinge shaft 202 may be structured such that the eyelet ring 222 (and its tab 244) is positioned in approximately the middle of the hinge shaft 202 along its longitudinal axis, but the eyelet ring 222 could be positioned at other locations along the length of the hinge shaft 202.

The distal end 248 of the proximal shaft 218 may include a distal extension (not shown) which is received in the proximal end 250 of the distal shaft 220. For example, the distal extension may be in the form of a sleeve which extends through the eyelet ring 222 and is press fit within the open interior of the proximal end 250 of the distal shaft 220. The hinge shaft 202 may thus be assembled by advancing the distal extension of the proximal shaft 218 through the eyelet ring 222 and into the open proximal end of the distal shaft 220. The proximal shaft 218 is preferably not advanced too far into the distal shaft 220, so that the eyelet ring 222 received therebetween will not be compressed and have difficulty rotating freely about the longitudinal axis of the hinge shaft 202. Once the proximal shaft 218 is properly received by the distal shaft 220, the position of the shafts 218, 220 may be secured by inserting one or more pins 252 through respective aligned bores passing through the overlapping walls of the proximal and distal shafts 218, 220. In one example, four such pins 252 are used for each hinge shaft 202, spaced at 90° intervals about the longitudinal axis.

After the pins 252 are inserted, they are welded and blended within the bores until the outer surface of the hinge shaft 202 extending over the pins 252 is smooth.

Figure 11A:
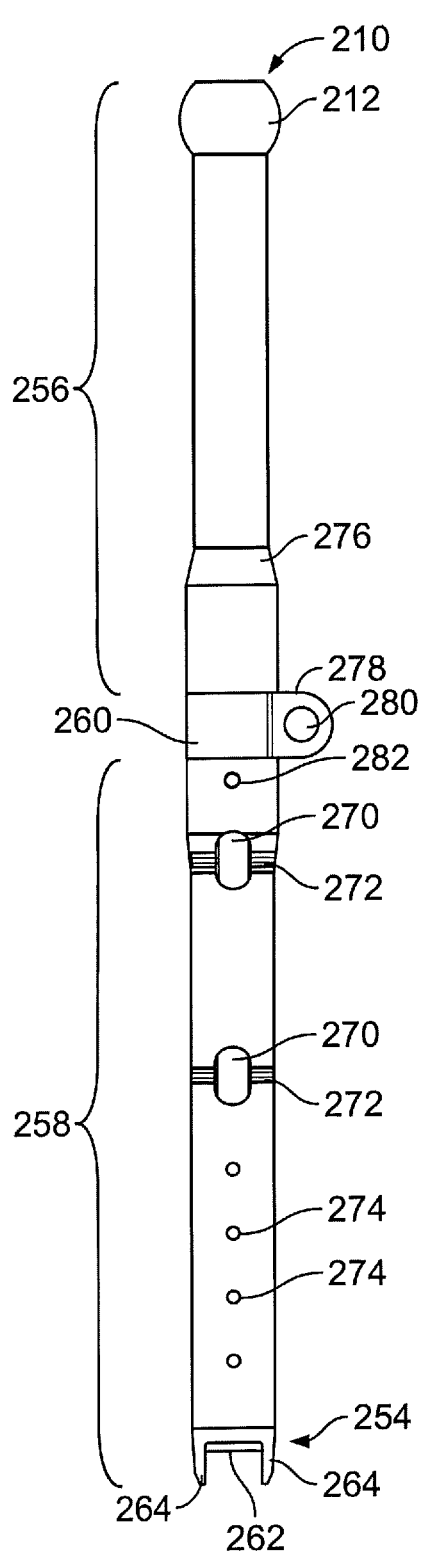
FIGS. 11A-B are elevational views of a ball shaft of the compression and distraction system of FIGS. 9A-B.
Figure 11B:
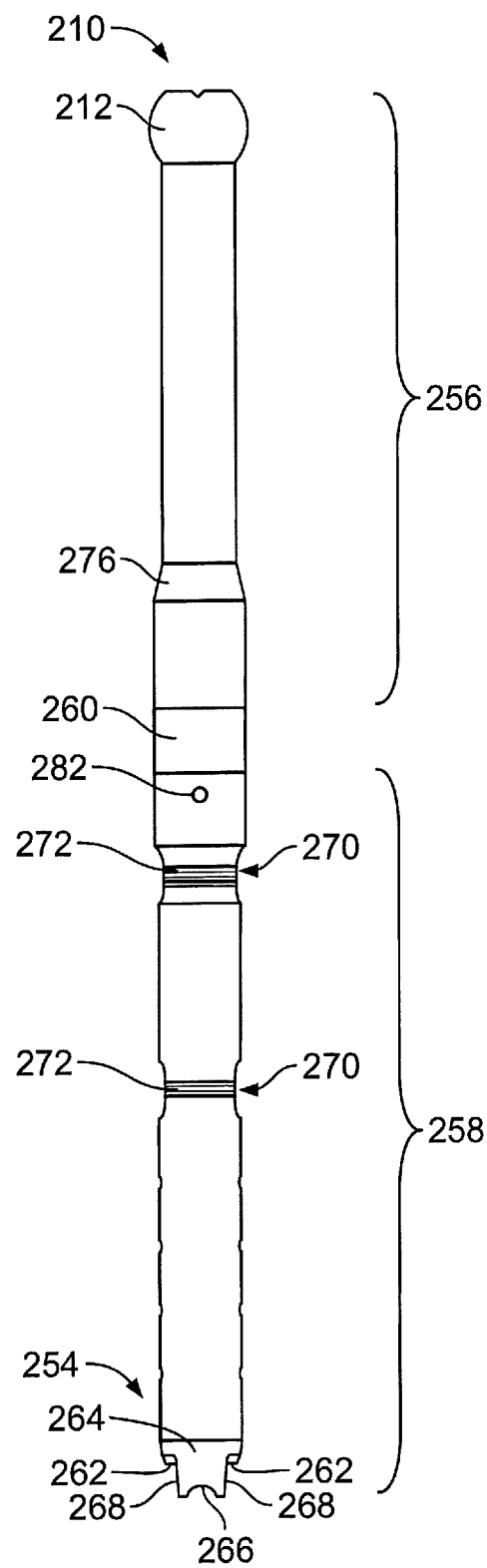

FIGS. 11A-B illustrate elevational views of the ball shaft 204, taken along orthogonal directions. The ball shaft 204 has a proximal end 210 and a distal end 254, with the ball 212 being at the proximal end 210. The ball shaft 204 includes a proximal shaft 256 and a distal shaft 258, with an eyelet ring 260 disposed therebetween. The ball shaft 204 includes numerous structures which are similar or identical to corresponding structures of the hinge shaft 202. For example, the distal shaft 258 and the eyelet ring 260 of the ball shaft 204 may be identical to the respective distal shaft 220 and eyelet ring 222 of the hinge shaft 202.

As with the distal shaft 220 of the hinge shaft 202, the distal shaft 258 of the ball shaft 204 may have a similar structure to the body 110 of the counter torque tube 108. That is, the distal shaft 258 desirably has a tubular shape with an open interior designed to receive a passageway device 31 therein. The open interior may have the same grooved structure as the counter torque tube 108, in order to similarly receive and constrain the blades 56 of the passageway device 31. The distal end 254 may also have the same structure for engaging the cage 42 of a connecting element 30 as the distal end 114 of the counter torque tube body 110 or the distal end 216 of the hinge shaft 202. That is, the distal end 254 may have a chamfered distal edge 262 arranged to abut the proximal end 54 of the cage 42 of the connecting element 30 when the ball shaft 204 is fully advanced against the cage 42. The distal end 254 may also include opposing extensions 264 with a cut out 266 shaped to abut the rod 44 and/or edges 268 for engaging the respective edges 143 of the arms 58 of the cage 42. Also, the distal shaft 258 may include one or more windows 270 and one or more laser markings, such as lines 272, arranged in the same manner as described above with respect to the counter torque tube 108 or the hinge shaft 202, such that the full and proper advancement of the ball shaft 204 can be determined based on alignment with the proximal edges 144 of the blades 56. The distal shaft 258 may also include one or more holes 274 along at least a portion of the length of the distal shaft 258, preferably in alignment with the grooves in its interior surface. Such holes 274 are desirably sized and positioned in the same manner as the holes 150 in the counter torque tube 108 or the holes 236 in the hinge shaft 202, in order to similarly release any trapped fluid and/or tissue.

The proximal shaft 256 of the ball shaft 204 may be narrower along at least a portion of its length, in order to reduce weight and material, and thus proximal shaft 256 may include a tapered portion 276. The ball 212 is a generally spherical component sized to fit within the hinge 208 to form the polyaxial fulcrum 214. The proximal shaft 256 preferably includes a passageway along its length that is open at each end of the proximal shaft 218 and that communicates with the open interior of the distal shaft 258. In that way, a tool, such as the set screw driver 104, can be passed down within the ball shaft 204 through the open proximal end 210 in order to lock the position of the connecting element 30 with respect to the rod 44 by tightening the set screw 45.

An eyelet ring 260 is located between the proximal shaft 256 and the distal shaft 258. The eyelet ring 260 includes a laterally extending tab 278 having a bore 280 formed within it. The bore 280 is configured to receive a portion of one or more compression or distraction tools, as discussed below. Although the bore 280 may have an hourglass shape along its central axis, as disclosed in the '809 Patent, the bore 280 may alternatively have another shape, such as a substantially cylindrical shape along its central axis. The eyelet ring 260 is rotatable about the longitudinal axis of the ball shaft 204, such that the angular position of the tab 278 around the ball shaft 204 can be varied. The ball shaft 204 may be structured such that the eyelet ring 260 (and its tab 278) is positioned in approximately the middle of the ball shaft 204 along its longitudinal axis, but the eyelet ring 260 could be positioned at other locations along the length of the ball shaft 204.

The ball shaft 204 may be assembled in the same manner as the hinge shaft 202. In particular, the proximal shaft 256 may be press fit or otherwise received within the distal shaft 258, and then the position of the shafts 256, 258 may be secured by inserting one or more pins 282 through respective aligned bores passing through the overlapping walls of the proximal and distal shafts 256, 258. Four such pins 282 may be inserted into the ball shaft 204, spaced at 90° intervals about the longitudinal axis, after which the pins 282 may be welded and blended within the bores until the outer surface of the ball shaft 204 extending over the pins 282 is smooth.

Figure 12A:
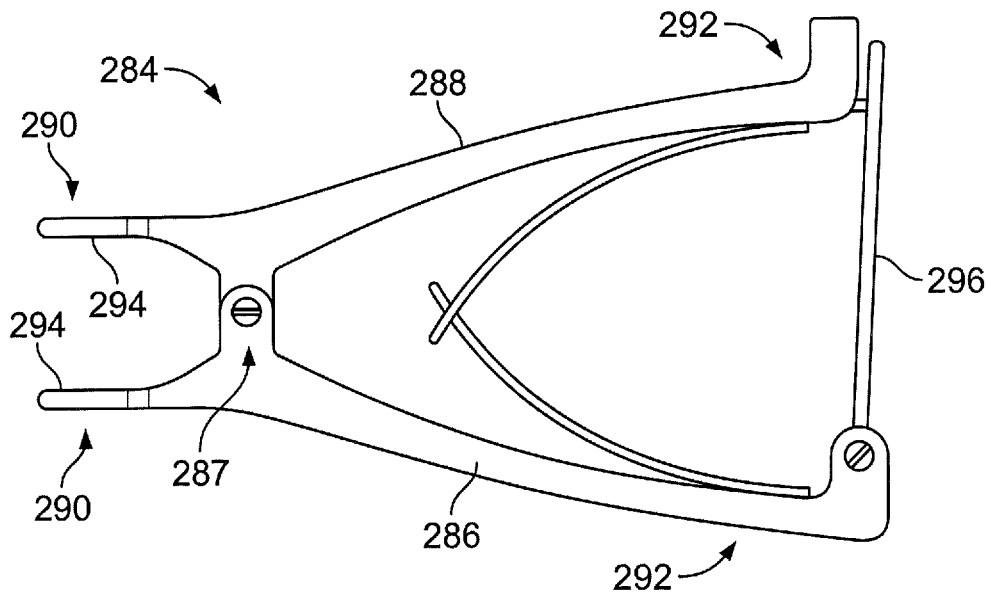
FIG. 12A is a plan view of a distractor for use with a compression and distraction system in accordance with an embodiment of the present invention.

FIG. 12A illustrates an embodiment of a distractor 284 for use in conjunction with the present invention. The distractor 284 may be identical in structure and function to the distraction pliers disclosed in the '809 Patent. For example, the distractor 284 may include a first handle 286 and a second handle 288 pivotably connected together at a pivot point 287. Each of the first and second handles 286, 288 has a tip end 290 and a ratchet end 292. A tip 294, which may have a generally cylindrical shape, is formed at the tip end 290 of each handle 286, 288, and a ratchet 296 for locking the distraction position of the distractor 284 extends between the handles 286, 288 at the ratchet end 292.

Figure 13A:
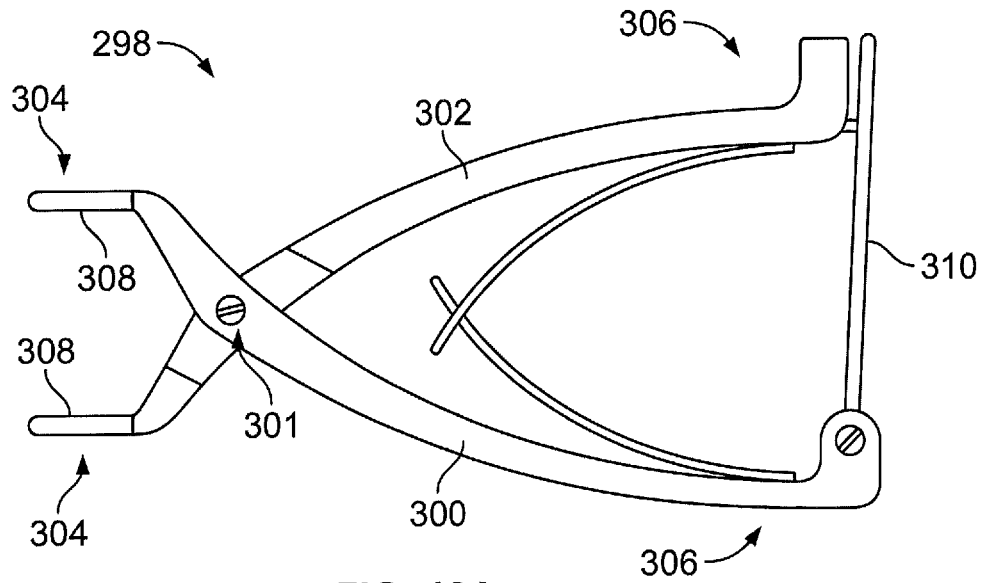
FIG. 13A is a plan view of a compressor for use with a compression and distraction system in accordance with an embodiment of the present invention.

FIG. 13A illustrates an embodiment of a compressor 298 for use in conjunction with the present invention. The compressor 298 may be identical in structure and function to the compression pliers disclosed in the '809 Patent. For example, the compressor 298 may include a first handle 300 and a second handle 302 pivotably connected together at a pivot point 301. Each of the first and second handles 300, 302 has a tip end 304 and a ratchet end 306. A tip 308, which may have a generally cylindrical shape, is formed at the tip end 304 of each handle 300, 302, and a ratchet 310 for locking the compression position of the compressor 298 extends between the handles 300, 302 at the ratchet end 306.

One method of using the compression and distraction system 200 is by inserting the hinge shaft 202 and the ball shaft 204 over and along respective passageway devices 31 associated with connecting elements 30 attached to the vertebrae 24, 26 that the surgeon or other user desires to move relative to one another. It is noted that the hinge shaft 202 and ball shaft 204 can be inserted without regard to the orientation of the tabs 244, 278 of the respective eyelet rings 222, 260. Indeed, because the eyelet rings 222, 260 are rotatable about the longitudinal axes of the respective hinge shaft 202 and ball shaft 204, the tabs 244, 278 can be properly oriented after the hinge shaft 202 and ball shaft 204 are inserted. In order to align the tabs 244, 278, the ring 222 of the hinge shaft 202 is rotated until the tab 244 is directed away from the ball shaft 204 along the cephalad or caudal direction 12, 14, and the ring 260 of the ball shaft 204 is rotated until the tab 278 is directed away from the hinge shaft 202 along the cephalad or caudal direction 12, 14, as shown in FIGS. 9A-B. Similarly, the hinge shaft 202 and ball shaft 204 can desirably be inserted without regard to the orientation of the hinge 208 of the hinge shaft 202. That is, the hinge 208 is preferably symmetrical, such that it can engage the ball 212 of the ball shaft 204 (whether the ball shaft 202 is displaced in the cephalad direction 12 or the caudal direction 14 from the hinge shaft 202) by rotating the hinge 208 about the proximal end 206 of the hinge shaft 202 and towards the ball shaft 204 in either the cephalad direction 12 or the caudal direction 14. Thus, after the hinge shaft 202 and ball shaft 204 are inserted, the hinge 208 is rotated about the proximal end 206 of the hinge shaft 202 until the ball 212 of the ball shaft 204 is received within the hinge 208 as shown in FIG. 9B. Next, the hinge shaft 202 and ball shaft 204, and the associated vertebrae 24, 26, are distracted apart using the distractor 284 or compressed towards one another using the compressor 298, as shown in FIGS. 12B and 13B, respectively, and discussed below.

Figure 12B:
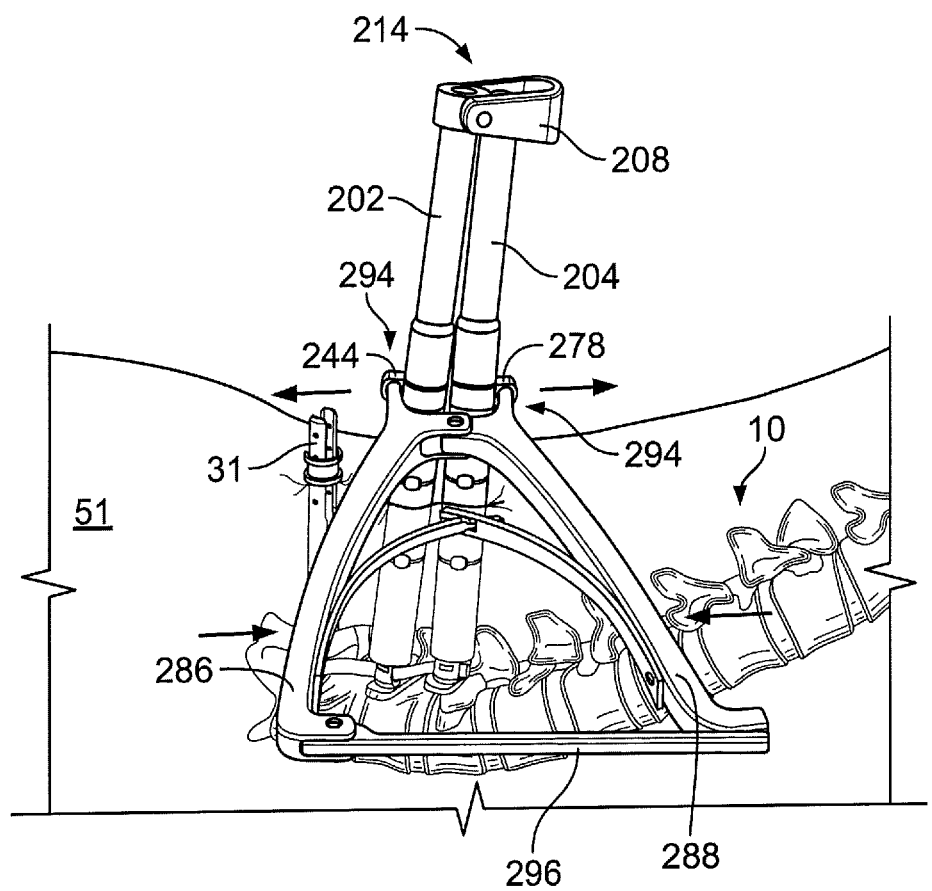
FIG. 12B is a perspective view of the distractor of FIG. 12A being used with the components of the compression and distraction system in the configuration of FIG. 9B.

FIG. 12B illustrates the distractor 284 engaging the hinge shaft 202 and the ball shaft 204 to distract apart the vertebrae 24, 26 connected thereto. In particular, the tips 294 of the distractor 284 are inserted into respective bores 246, 280 of the hinge shaft 202 and ball shaft 204, respectively. Then, the handles 286, 288 are pressed together, which causes the tips 294 to move away from each other. The hinge shaft 202 and ball shaft 204 are thus caused to pivot about the polyaxial fulcrum 214 such that the distal ends 216, 254 of the respective hinge shaft 202 and ball shaft 204 separate the respective connecting elements 30 and distract the associated vertebrae 24, 26. Once the first and second handles 286, 288 are pressed to impart an appropriate amount of distraction to the vertebrae, they are locked in that position by the ratchet 296. The vertebrae 24, 26 may then be held in that position by the distractor 284 until the surgeon or other user fixes the relative positions of the vertebrae 24, 26. That fixation may be performed by inserting a tool, such as the set screw driver 104, through each of the hinge shaft 202 and ball shaft 204, and then tightening a set screw 45 against the rod 44 in each of the connecting elements 30 connected to the vertebrae 24, 26 to be fixed.

Figure 13B:
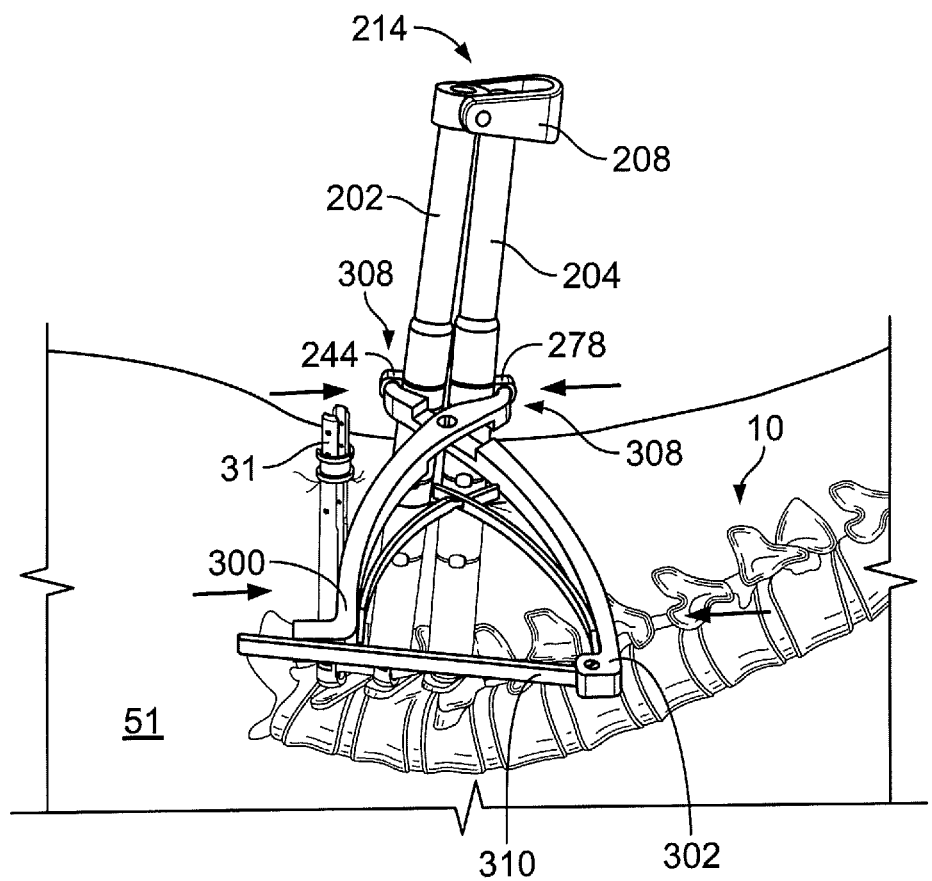
FIG. 13B is a perspective view of the compressor of FIG. 13A being used with the components of the compression and distraction system in the configuration of FIG. 9B.

FIG. 13B illustrates the compressor 298 engaging the hinge shaft 202 and the ball shaft 204 to compress together the vertebrae 24, 26 connected thereto. In particular, the tips 308 of the compressor 298 are inserted into respective bores 246, 280 of the hinge shaft 202 and ball shaft 204, respectively. Then, the handles 300, 302 are pressed together, which causes the tips 308 to move towards each other. The hinge shaft 202 and ball shaft 204 are thus caused to pivot about the polyaxial fulcrum 214 such that the distal ends 216, 254 of the respective hinge shaft 202 and ball shaft 204 move the respective connecting elements 30 closer together and compress the associated vertebrae 24, 26. Once the first and second handles 300, 302 are pressed to impart an appropriate amount of compression to the vertebrae, they are locked in that position by the ratchet 310. The vertebrae 24, 26 may then be held in that position by the compressor 298 until the surgeon or other user fixes the relative positions of the vertebrae 24, 26. That fixation may be performed by inserting a tool, such as the set screw driver 104, through each of the hinge shaft 202 and ball shaft 204, and then tightening a set screw 45 against the rod 44 in each of the connecting elements 30 connected to the vertebrae 24, 26 to be fixed.

If performing final tightening of a set screw 45 into a connecting element 30 to which a hinge shaft 202 or a ball shaft 204 are connected, the counter torque tube 108 can be advanced against the cage 42 of an adjacent vertebra to help reduce the amount of torque that is transmitted to the spine 10.

During compression or distraction, the eyelet rings 222, 260 may rotate about the respective longitudinal axes of the hinge shaft 202 and ball shaft 204 while engaged with the tips 294, 308 of the respective compressor 298 or distractor 284. That is, if the bores 246, 280 of the respective eyelet rings 222, 260 have a substantially cylindrical rather than an hourglass shape along their central axes, as discussed above, such rotation may permit the tips 294, 308 to follow an arcuate path about the pivot points 287, 301 of the respective compressor 298 or distractor 284. Also, during the compression or distraction, the connecting elements 30 connected to the hinge shaft 202 and ball shaft 204 may move with respect to the rod 44 as the connecting elements 30 are displaced relative to one another. In one alternative, one of the set screws 45 (either the one associated with the connecting element 30 connected to the hinge shaft 202 or the one associated with the connecting element connected to the ball shaft 204) may be tightened against the rod 44 before compression or distraction is performed. In that way, a one-way displacement may be induced, where the non-tightened connecting element 30 is moved along the rod 44 during compression or distraction.

After completing compression or distraction between two adjacent vertebrae 24, 26, the compression and distraction system 200 may be used to perform compression or distraction between two other vertebrae (e.g., one vertebra 24 previously engaged for compression/distraction and the next adjacent vertebra 22). In that case, the entire compression and distraction system 200 need not be removed from the body. Rather, one of the hinge shaft 202 or ball shaft 204 may be moved to that next adjacent vertebra 22, and the tabs 244, 278 may be rotated accordingly, and the hinge 208 may be flipped to engage the ball 212 of the ball shaft 204. For example, with reference to FIGS. 9A-B, after compression or distraction is completed between vertebrae 24 and 26, the ball shaft 24 may be repositioned over and along the passageway device 31 connected to vertebra 22. Then the ring 222 of the hinge shaft 202 is rotated until the tab 244 is directed away from the ball shaft 204 along the cephalad or caudal direction 12, 14, and the ring 260 of the ball shaft 204 is rotated until the tab 278 is directed away from the hinge shaft 202 along the cephalad or caudal direction 12, 14. The hinge 208 can then be rotated about the proximal end 206 of the hinge shaft 202 in the caudal direction 14 and into engagement with the ball 212 of the ball shaft 204. Compression or distraction can then be performed between the vertebrae 22, 24 as described above.

After the various set screws 45 are finally tightened into the cages 42, the passageway devices 31 can be detached from the respective connecting elements 30 and removed from the body. For example, the blades 56 of the passageway devices 31 may be separately disconnected from the connecting elements 30 and removed from the body. If monolithic blade-screws 60 were used, the blades 56 may be disconnected from the connecting element 30 by breaking each of the blades 56 away from the connecting element 30 at the frangible portions 62.

Figure 14A:
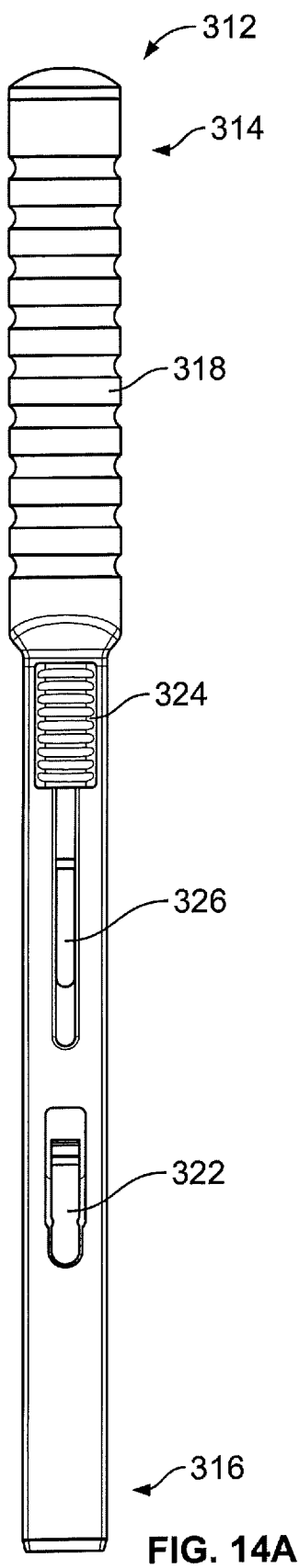
FIG. 14A is an elevational view of a blade remover, in accordance with an embodiment of the present invention.

One method for breaking the blades 56 of the blade-screw 60 away from the connecting element 30 is by using a blade remover 312, illustrated in FIG. 14A. The blade remover 312 is an elongate tool having a proximal end 314 and a distal end 316. The blade remover 312 may include a handle 318 at the proximal end 314 and may have a channel (not shown) formed therein open to the distal end 316. The channel may be constructed to receive a blade 56 of a blade-screw 60 therein. The blade remover 312 may also include a window and a laser marking (not shown) (or multiple windows and laser markings, if multiple blades 56 with different lengths are used), as described above with respect to the counter torque tube 108, the hinge shaft 202, and the ball shaft 204, in order to determine whether the blade remover 312 has been fully and properly advanced along the blade 56. The blade remover 312 may include a spring clip 322 in communication with the channel such that the spring clip 222 securely engages a blade 56 when the blade 56 is positioned within the channel, preferably in order to retain the blade 56 within the blade remover 312 after the blade 56 has been detached from the connecting element 30. The blade remover 312 may also include a release mechanism for ejecting the blade 56 from the channel after the detached blade 56 has been removed from the body. That release mechanism may include a slider 324 received within a longitudinal track, such as a slot 326, extending along the blade remover 312. The release mechanism is structured such that distal movement of the slider 324 along the track will push the blade 56 out of the channel at the distal end 316 of the blade remover 312.

Figure 14D:
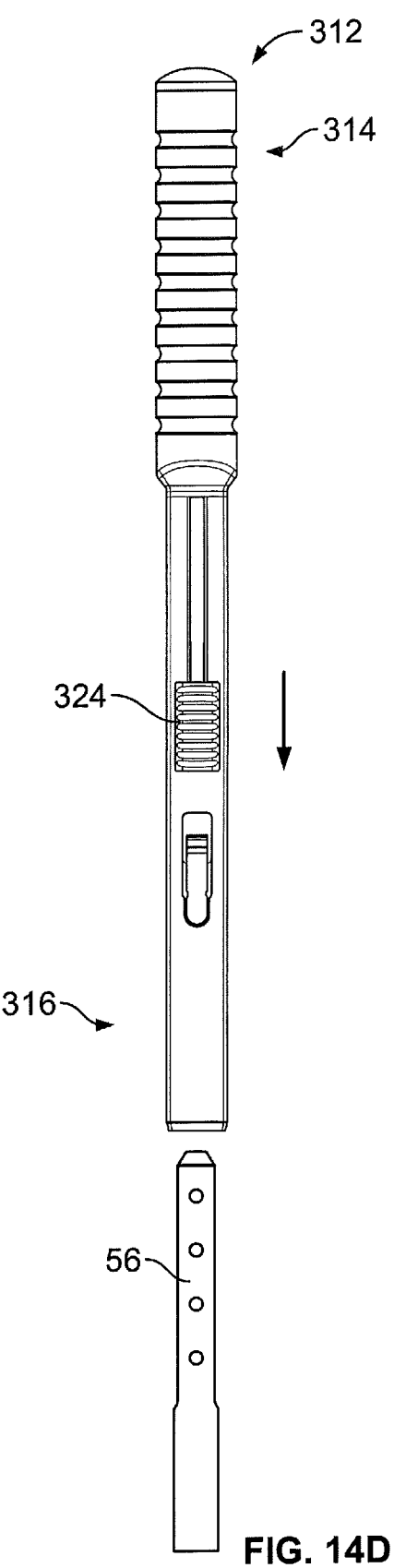
FIG. 14D is an elevational view of the blade remover of FIG. 14A ejecting a blade of a blade-screw, in accordance with an embodiment of the present invention.
Figure 14B:
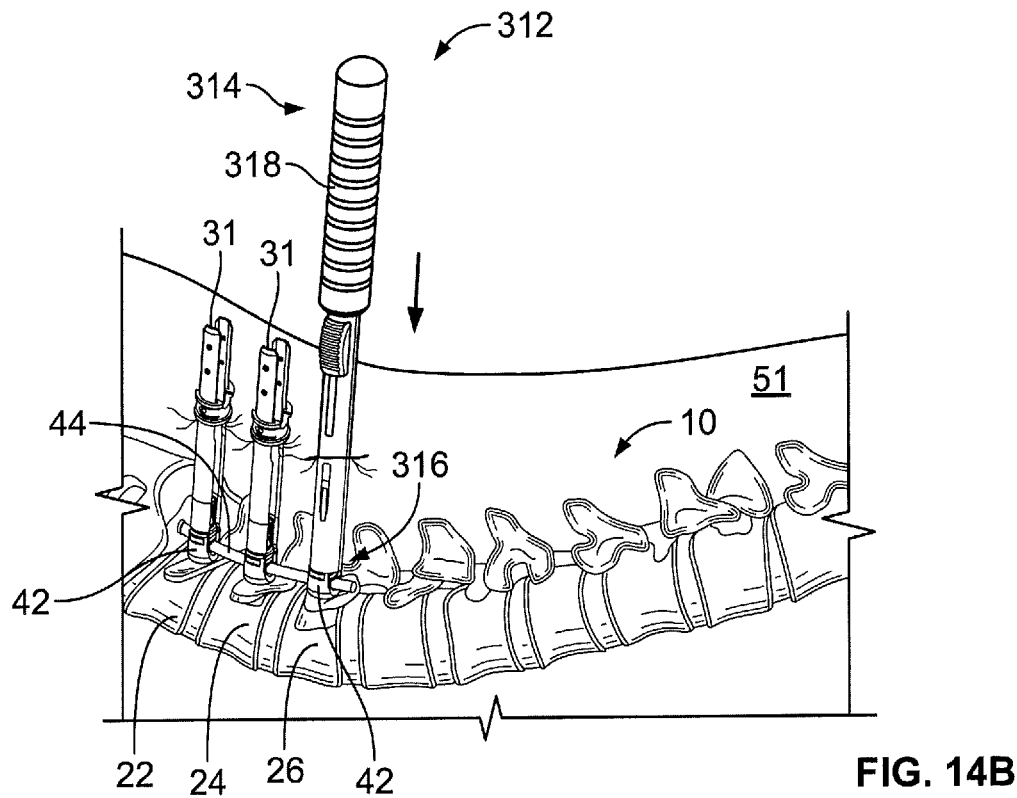
FIGS. 14B-C are perspective views of the blade remover of FIG. 14A being used with the system of blade-screws of FIG. 1.
Figure 14C:
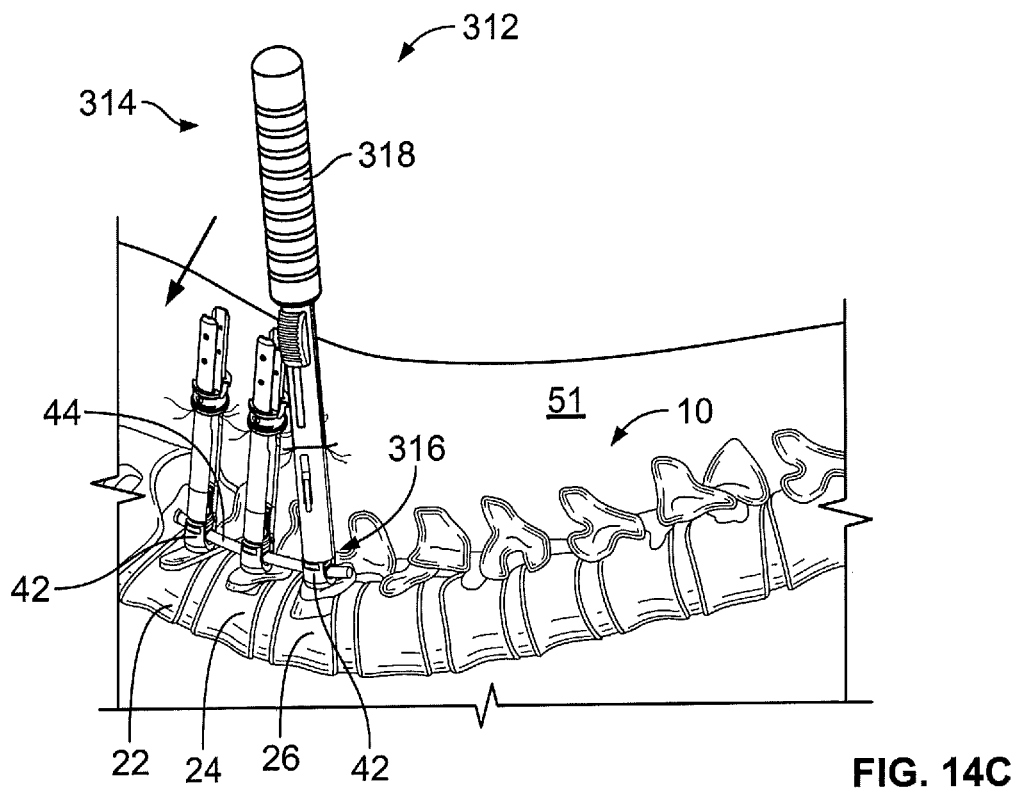

In use, the blade remover 312 is engaged to a blade 56 by sliding the blade remover 312 distally over the blade 56 until the blade is received within the channel, as illustrated in FIG. 14B. Using the handle 318, a surgeon or other user may pivot the blade remover 312, and thus the blade 56 received therein, about the frangible portion 62 until the frangible portion 62 fractures, thus disconnecting the blade 56 from the connecting element 30. As illustrated in FIG. 14C, each blade 56 may be pivoted away from the adjacent blade 56 of the same blade-screw 60. The blade remover 312 may then be removed from the body, and desirably the spring clip 322 may retain the blade 56 within the blade remover 312 until the blade remover 312 is removed from the body. After the blade remover 312 is removed from the body, the detached blade 56 may be ejected from the channel by actuating the release mechanism. As shown in FIG. 14D, the slider 324 is moved distally along the blade remover 312 until the blade 56 is ejected from the distal end 316 of the blade remover 312. The blade remover 312 may then be used again by repeating the above steps to remove other blades 56 from the connecting elements 30.

If one or both blades 56 of one of the passageway devices 31 were to become prematurely disconnected from a connecting element 30, and further access to the connecting element 30 is desired, one or more of the blade rescue retractors of the blade rescue system disclosed in the '098 Application may be used as functional replacements for the missing blade(s), as disclosed in that application. In order to ease the insertion of such a blade rescue retractor into the body, a series of sequential dilators may be inserted to gently enlarge a path to the targeted connecting element 30, with the largest of the dilators being sized to receive one of the blade rescue retractors inside of it. Thereafter, all but the largest of the sequential dilators may be removed, and then the blade rescue retractor may be advanced within the largest dilator to the connecting element 30. After the blade rescue retractor reaches the connecting element 30, the largest dilator may be removed from the body.

Although various components described herein, such as the counter torque tube 108, the hinge shaft 202, and the ball shaft 204, have been described and illustrated as being designed to interact with the blades 56 of passageway devices 31, it is to be understood that those components could be designed to interact with different types of passageway devices, such as cannulas, towers, or portals, some of which may not have blades 56. In such cases, those components may be designed to interact similarly with those other types of passageway devices. For example, the open interiors of the counter torque tube 108, hinge shaft 202, and ball shaft 204 may be structured to receive such other type of passageway device, and the interior surfaces of those components may have recessed grooves that have a correspondingly different shape, or the interior surfaces may have other structures for receiving or otherwise engaging corresponding structures of the passageway device. Moreover, the windows and the laser markings (e.g., lines) may be designed to align with a predetermined portion of the passageway device, such as the proximal end of the passageway device.

The various components described herein are preferably constructed of materials safe for use in the body. In one embodiment, many of the components to be permanently implanted in the body, such as the blade-screws 60 and the rod 44, may be constructed from titanium or a titanium alloy. In one alternative, some or all of such permanently implantable components may be constructed from a cobalt-chromium alloy, such as the material sold under the trademark VITALLIUM® by Howmedica Osteonics Corp. Many or all of the instruments for use in implanting and manipulating the permanently implantable components, such as the rod inserter 84, the counter torque tube 108, the blade remover 312, and the components of the compression and distraction system 200 (including the hinge shaft 202, the ball shaft 204, the distractor 284, and the compressor 298), may be entirely, largely, or partially constructed from stainless steel.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of manipulating portions of a spinal fusion system, comprising:
   connecting a distal end of a first shaft to a first connecting element affixed to a first vertebra of a spine, the first shaft including a first connector, the first connector being rotatable about a longitudinal axis of the first shaft;
   connecting a distal end of a second shaft to a second connecting element affixed to a second vertebra of the spine, the second shaft including a second connector; and
   manipulating a manipulation device connected to the first and second connectors so as to move the first and second shafts with respect to one another to induce relative movement between the first and second vertebrae, wherein the first connector rotates about the longitudinal axis of the first shaft during the manipulating step.

2. The method of claim 1, wherein the second connector is rotatable about a longitudinal axis of the second shaft.

3. The method of claim 1, wherein the manipulating step comprises pivoting a first arm of the manipulation device with respect to a second arm of the manipulation device, the first arm being connected to the first connector and the second arm being connected to the second connector.

4. The method of claim 3, wherein, during the manipulating step, the longitudinal axis of the first shaft extends along an anterior-posterior direction, and wherein the manipulating step comprises pivoting the first arm of the manipulation device with respect to the second arm of the manipulation device about a pivot axis extending along the anterior-posterior direction.

5. The method of claim 1, wherein the first vertebra is located on a first side of the second vertebra, further comprising the following steps, all while maintaining the distal end of the second shaft connected to the second connecting element:
   disconnecting the distal end of the first shaft from the first connecting element;
   repositioning the first shaft on a second side of the second vertebra opposite the first side; and
   connecting the distal end of the first shaft to a third connecting element affixed to a third vertebra, the third vertebra being located on the second side of the second vertebra.

6. The method of claim 5, further comprising rotating the second connector of the second shaft towards the first shaft connected to the third connecting element, while maintaining the distal end of the second shaft connected to the second connecting element.

7. The method of claim 5, further comprising connecting the manipulation device to the first and second connectors, while maintaining the distal end of the second shaft connected to the second connecting element.

8. The method of claim 5, further comprising disconnecting a proximal end of the first shaft from a proximal end of the second shaft before the repositioning step, while maintaining the distal end of the second shaft connected to the second connecting element.

9. The method of claim 8, further comprising reconnecting the proximal end of the first shaft with the proximal end of the second shaft after the repositioning step, while maintaining the distal end of the second shaft connected to the second connecting element.

10. The method of claim 9, wherein the step of disconnecting the proximal end of the first shaft from the proximal end of the second shaft comprises uncoupling a receiver element at the proximal end of the second shaft from an engagement end at the proximal end of the first shaft, and wherein the reconnecting step comprises reorienting the receiver element and coupling the receiver element to the engagement end.

11. The method of claim 10, wherein reorienting the receiver element comprises rotating the receiver element from the first side to the second side of the second vertebra.

12. The method of claim 1, wherein the first connector is positioned in a middle portion of the first shaft between the distal end of the first shaft and a proximal end of the first shaft, and wherein the second connector is positioned in a middle portion of the second shaft between the distal end of the second shaft and a proximal end of the second shaft.

13. The method of claim 1, further comprising:
   receiving a first passageway device within the first shaft, the first passageway device extending proximally from the first connecting element; and
   receiving a second passageway device within the second shaft, the second passageway device extending proximally from the second connecting element.

14. The method of claim 13, wherein the step of receiving the first passageway device within the first shaft comprises receiving the first passageway device within an open interior portion of the first shaft such that a feature of the first passageway device is alignable with an opening through a sidewall of the first shaft to permit a view of the feature through the opening, the opening being positioned between a proximal end and the distal end of the first shaft.

15. The method of claim 14, wherein the feature is a proximal end of the first passageway device.

16. The method of claim 1, further comprising connecting a proximal end of the first shaft to a proximal end of the second shaft.

17. The method of claim 16, wherein the proximal ends of the first and second shafts are connected such that, during the manipulating step, the first and second shafts pivot about a pivot point proximate the proximal ends of the first and second shafts.

18. The method of claim 1, wherein the manipulating step comprises changing an orientation of a first arm of the manipulation device about the longitudinal axis of the first shaft while the first arm is connected to the first connector.

* * * * *